United States Patent
Norcross

(10) Patent No.: US 7,273,865 B2
(45) Date of Patent: Sep. 25, 2007

(54) THIAZOLOPYRIDINE

(75) Inventor: Roger David Norcross, Rheinfelden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 472 days.

(21) Appl. No.: 10/941,708

(22) Filed: Sep. 15, 2004

(65) Prior Publication Data

US 2005/0065151 A1 Mar. 24, 2005

(30) Foreign Application Priority Data

Sep. 19, 2003 (EP) .................... 03021119

(51) Int. Cl.
- *A61K 31/5377* (2006.01)
- *A61K 31/437* (2006.01)
- *C07D 413/14* (2006.01)
- *C07D 513/02* (2006.01)

(52) U.S. Cl. .................. 514/234.2; 544/106; 544/111; 544/125; 544/127; 514/231.2; 514/233.8; 514/299; 514/301; 546/112; 546/114

(58) Field of Classification Search ................ 544/106, 544/111, 125, 127; 546/112, 114; 514/231.2, 514/233.5, 233.8, 234.2
See application file for complete search history.

(56) References Cited

FOREIGN PATENT DOCUMENTS

| WO | WO 01/97786 A | 12/2001 |
|---|---|---|
| WO | WO 03/043634 A | 5/2003 |
| WO | WO 03/043636 A | 5/2003 |
| WO | WO 03/045386 A | 6/2003 |
| WO | WO 03/049741 A | 6/2003 |
| WO | WO 03/053946 A | 7/2003 |
| WO | WO 03/053954 A | 7/2003 |
| WO | WO 03/053961 A | 7/2003 |

OTHER PUBLICATIONS

Buchwald et al., Org. Letters, 4, pp. 973-976 (2002).

*Primary Examiner*—Golam M. M. Shameem
(74) *Attorney, Agent, or Firm*—George W. Johnston; Patricia S. Rocha-Tramaloni; Gene J. Yao

(57) ABSTRACT

The present invention relates to compounds of formula I

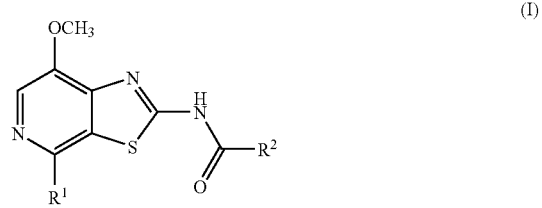

(I)

wherein $R^1$ and $R^2$ are described hereinbelow. These compounds have high affinity to $A_{2A}$ receptors and good selectivity to $A_1$ and $A_3$ receptors. These compounds are useful, inter alia, in the treatment of Alzheimer's disease, depression, Parkinson's disease and ADHD.

16 Claims, No Drawings

THIAZOLOPYRIDINE

FIELD OF THE INVENTION

The present invention relates to compounds of formula I

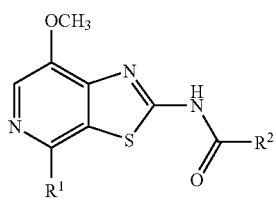

wherein $R^1$ and $R^2$ are described hereinbelow. These compounds have high affinity to $A_{2A}$ receptors and good selectivity to $A_1$ and $A_3$ receptors. These compounds are useful, inter alia, in the treatment of Alzheimer's disease, depression, Parkinson's disease and ADHD.

BACKGROUND OF THE INVENTION

Adenosine modulates a wide range of physiological functions by interacting with specific cell surface receptors. The potential of adenosine receptors as drug targets was first reviewed in 1982. Adenosine is related both structurally and metabolically to the bioactive nucleotides adenosine triphosphate (ATP), adenosine diphosphate (ADP), adenosine monophosphate (AMP) and cyclic adenosine monophosphate (cAMP); to the biochemical methylating agent S-adenosyl-L-methione (SAM); and structurally to the coenzymes NAD, FAD and coenzyme A; and to RNA. Together adenosine and these related compounds are important in the regulation of many aspects of cellular metabolism and in the modulation of different central nervous system activities.

The receptors for adenosine have been classified as $A_1$, $A_{2A}$, $A_{2B}$ and $A_3$ receptors, belonging to the family of G protein-coupled receptors. Activation of adenosine receptors by adenosine initiates signal transduction mechanism. These mechanisms are dependent on the receptor associated G protein. Each of the adenosine receptor subtypes has been classically characterized by the adenylate cyclase effector system, which utilizes cAMP as a second messenger. The $A_1$ and $A_3$ receptors, coupled with Gi proteins inhibit adenylate cyclase, leading to a decrease in cellular cAMP levels, while $A_{2A}$ and $A_{2B}$ receptors couple to $G_s$ proteins and activate adenylate cyclase, leading to an increase in cellular cAMP levels. It is known that the $A_1$ receptor system includes the activation of phospholipase C and modulation of both potassium and calcium ion channels. The $A_3$ subtype, in addition to its association with adenylate cyclase, also stimulates phospholipase C and so activates calcium ion channels.

The $A_1$ receptor (326-328 amino acids) was cloned from various species (canine, human, rat, dog, chick, bovine, guinea-pig) with 90-95% sequence identify among the mammalian species. The $A_{2A}$ receptor (409-412 amino acids) was cloned from canine, rat, human, guinea pig and mouse. The $A_{2B}$ receptor (332 amino acids) was cloned from human and mouse with 45% homology of human $A_{2B}$ with human $A_1$ and $A_{2A}$ receptors. The $A_3$ receptor (317-320 amino acids) was cloned from human, rat, dog, rabbit and sheep.

The $A_1$ and $A_{2A}$ receptor subtypes are proposed to play complementary roles in adenosine's regulation of the energy supply. Adenosine, which is a metabolic product of ATP, diffuses from the cell and acts locally to activate adenosine receptors to decrease the oxygen demand ($A_1$) or increase the oxygen supply ($A_{2A}$) and so reinstate the balance of energy supply: demand within the tissue. The actions of both subtypes are to increase the amount of available oxygen to tissue and to protect cells against damage caused by a short term imbalance of oxygen. One of the important functions of endogenous adenosine is preventing damage during traumas such as hypoxia, ischaemia, hypotension and seizure activity.

Furthermore, it is known that the binding of the adenosine receptor agonist to mast cells expressing the rat $A_3$ receptor resulted in increased inositol triphosphate and intracellular calcium concentrations, which potentiated antigen induced secretion of inflammatory mediators. Therefore, the $A_3$ receptor plays a role in mediating asthmatic attacks and other allergic responses.

Adenosine is a neuromodulator, able to modulate many aspects of physiological brain function. Endogenous adenosine, a central link between energy metabolism and neuronal activity, varies according to behavioral state and (patho) physiological conditions. Under conditions of increased demand and decreased availability of energy (such as hypoxia, hypoglycemia, and/or excessive neuronal activity), adenosine provides a powerful protective feedback mechanism. Interacting with adenosine receptors represents a promising target for therapeutic intervention in a number of neurological and psychiatric diseases such as epilepsy, sleep, movement disorders (Parkinson or Huntington's disease), Alzheimer's disease, depression, schizophrenia, or addiction. An increase in neurotransmitter release follows traumas such as hypoxia, ischaemia and seizures. These neurotransmitters are ultimately responsible for neural degeneration and neural death, which causes brain damage or death of the individual. The adenosine $A_1$ agonists which mimic the central inhibitory effects of adenosine may therefore be useful as neuroprotective agents.

Adenosine has been proposed as an endogenous anticonvulsant agent, inhibiting glutamate release from excitory neurons and inhibiting neuronal firing. Adenosine agonists therefore may be used as antiepileptic agents. Adenosine antagonists stimulate the activity of the CNS and have proven to be effective as cognition enhancers. Selective $A_{2a}$ antagonists have therapeutic potential in the treatment of various forms of dementia, for example in Alzheimer's disease, and of neurodegenerative disorders, e.g. stroke. Adenosine $A_{2a}$ receptor antagonists modulate the activity of striatal GABAergic neurons and regulate smooth and well-coordinated movements, thus offering a potential therapy for Parkinsonian symptoms. Adenosine is also implicated in a number of physiological processes involved in sedation, hypnosis, schizophrenia, anxiety, pain, respiration, depression, and drug addiction (amphetamine, cocaine, opioids, ethanol, nicotine, cannabinoids). Drugs acting at adenosine receptors therefore have therapeutic potential as sedatives, muscle relaxants, antipsychotics, anxiolytics, analgesics, respiratory stimulants, antidepressants, and to treat drug abuse. They may also be used in the treatment of ADHD (attention deficit hyperactivity disorder).

An important role for adenosine in the cardiovascular system is as a cardioprotective agent. Levels of endogenous adenosine increase in response to ischaemia and hypoxia, and protect cardiac tissue during and after trauma (preconditioning). By acting at the $A_1$ receptor, adenosine $A_1$ agonists may protect against the injury caused by myocardial ischemia and reperfusion. The modulating influence of $A_2a$ receptors on adrenergic function may have implications for a variety of disorders such as coronary artery disease and heart failure. $A_{2a}$ antagonists may be of therapeutic benefit in situations in which an enhanced antiadrenergic response is desirable, such as during acute myocardial ischemia. Selective antagonists at $A_{2a}$ receptors may also enhance the effectiveness of adenosine in terminating supraventricula arrhytmias.

Adenosine modulates many aspects of renal function, including renin release, glomerular filtration rate and renal blood flow. Compounds which antagonize the renal affects of adenosine have potential as renal protective agents. Furthermore, adenosine $A_3$ and/or $A_{2B}$ antagonists may be useful in the treatment of asthma and other allergic responses or and in the treatment of diabetes mellitus and obesity.

Numerous documents describe the current knowledge on adenosine receptors, for example the following publications: Bioorganic & Medicinal Chemistry, 6, (1998), 619-641; Bioorganic & Medicinal Chemistry, 6, (1998), 707-719; J. Med. Chem., (1998), 41, 2835-2845; J. Med. Chem., (1998), 41, 3186-3201; J. Med. Chem., (1998), 41, 2126-2133; J. Med. Chem., (1999), 42, 706-721; J. Med. Chem., (1996), 39, 1164-1171; Arch. Pharm. Med. Chem., 332, 39-41, (1999); Am. J. Physiol., 276, H1113-1116, (1999) and Naunyn Schmied, Arch. Pharmacol. 362, 375-381, (2000).

SUMMARY OF THE INVENTION

An aspect of the present invention is directed to the compounds of formula I

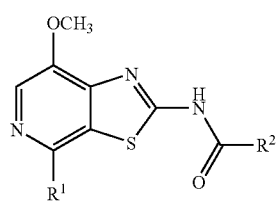

wherein,
$R^1$ is selected from morpholin-4-yl, phenyl and tetrahydropyran-4-yl;
$R^2$ is selected from
—$(CH_2)_n$-aryl;
—$(CH_2)_n$-aryl substituted by one or more substituents selected from the group consisting of halogen, lower alkoxy, lower alkyl, —$(CH_2)_n$NR'R", —$O(CH_2)_n$—O-lower alkyl, and —$(CH_2)_n$-heterocyclyl;
heteroaryl;
heteroaryl substituted by one or more substituents, selected from the group consisting of lower alkyl, lower alkoxy, —$(CH_2)_n$NR'R", —$(CH_2)_n$-heterocyclyl, and —$(CH_2)_n$-heterocyclyl substituted by one or more substituents selected from hydroxy, lower alkoxy, —$(CH_2)_n$—OH, —$(CH_2)_n$—O-lower alkyl and lower alkyl;
—$(CH_2)_n$-cycloalkyl;
—$(CH_2)_n$—O-lower alkyl;
NR'R";
benzo[1,3]dioxole;
2-methyl-1-oxo-2,8-diaza-spiro[4,5]decane;
2-oxa-5-aza-bicyclo[2.2.1]heptane; or
1-oxa-8-aza-spiro[4.5]decane;

R' and R" are independently from each other selected from lower alkyl, —$(CH_2)_n$—O-lower alkyl, cycloalkyl, and cycloalkyl substituted by hydroxy; and
n is 0, 1 or 2;

or a pharmaceutically acceptable salt thereof.

Other embodiments of this invention are directed to methods of manufacture of compounds of formula I, pharmaceutical compositions containing a compound of formula I, or a pharmaceutically acceptable salt thereof, as well as a method of controlling or prevention of illnesses based on the modulation of the adenosine system, such as Alzheimer's disease, Parkinson's disease, Huntington's disease, neuroprotection, schizophrenia, anxiety, pain, respiration deficits, depression, drug addiction, such as amphetamine, cocaine, opioids, ethanol, nicotine, cannabinoids, or against asthma, allergic responses, hypoxia, ischaemia, seizure and substance abuse comprising administering to a patient in need thereof a therapeutically effective amount of a compound of formula I or a pharmaceutically acceptable salt thereof.

Furthermore, compounds of the present invention are useful as sedatives, muscle relaxants, antipsychotics, antiepileptics, anticonvulsants and cardiaprotective agents for disorders such as coronary artery disease and heart failure. Preferred indications in accordance with the present invention are those that depend on the $A_{2A}$ receptor antagonistic activity and which include disorders of the central nervous system, for example the treatment or prevention of Alzheimer's disease, certain depressive disorders, drug addiction, neuroprotection and Parkinson's disease as well as ADHD.

DETAILED DESCRIPTION OF THE INVENTION

As used herein, the term "lower alkyl" refers to a saturated straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1-4 carbon atoms.

The term "halogen" refers to chlorine, iodine, fluorine and bromine.

The term "cycloalkyl" refers to a saturated carbocyclic group, containing 3-7 carbon atoms.

The term "aryl" refers to a monovalent cyclic aromatic hydrocarbon radical consisting of one or more fused rings in which at least one ring is aromatic in nature, for example phenyl, benzyl, naphthyl, biphenyl or indanyl.

The term "heteroaryl" refers to a monovalent aromatic heterocyclic radical, for example pyridyl, pyrazinyl, pyrimidinyl, triazinyl, thiazolyl, thienyl, furyl, pyrrolyl, imidazolyl or pyrazolyl.

The term "heterocyclyl" refers to a non aromatic cyclic hydrocarbon radical, containing at least one heteroatom, selected from the group consisting of N, O or S, for example azepanyl, oxetanyl, tetrahydrofuranyl, tetrahydropyranyl, azetidinyl, pyrrolidinyl, piperidinyl, piperazinyl, morpholinyl or thiomorpholinyl.

The term "hydroxy" refers to an —OH substituent.

The term "lower alkoxy" refers to a group wherein the alkyl residues is as defined above, and which is attached via an oxygen atom.

The term "pharmaceutically acceptable acid addition salts" refers to salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The term "therapeutically effective amount" refers to an amount of at least one compound of formula I, or a pharmaceutically acceptable salt thereof, that modulates adenosine.

In one embodiment, this invention relates to compounds of formula I

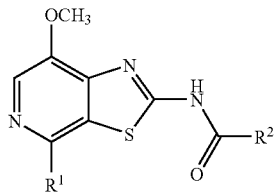

wherein,
R$^1$ is morpholin-4-yl; and
R$^2$ is —(CH$_2$)$_n$-aryl;
 —(CH$_2$)$_n$-aryl substituted by one or more substituents selected from the group consisting of halogen, lower alkoxy, lower alkyl, —(CH$_2$)$_n$NR'R", —O(CH$_2$)$_n$—O—lower alkyl, and —(CH$_2$)$_n$-heterocyclyl;
heteroaryl;
heteroaryl substituted by one or more substituents selected from the group consisting of lower alkyl, lower alkoxy, —(CH$_2$)$_n$NR'R", —(CH$_2$)$_n$-heterocyclyl substituted by hydroxy and or —(CH$_2$)$_n$-heterocyclyl substituted by lower alkoxy;
—(CH$_2$)$_n$-heterocyclyl;
—(CH$_2$)$_n$-heterocyclyl substituted by one or more substituents selected from the group consisting of —(CH$_2$)$_n$—OH, —(CH$_2$)$_n$—O-lower alkyl and lower alkyl;
—(CH$_2$)$_n$-cycloalkyl;
—(CH$_2$)$_n$—O-lower alkyl;
NR'R";
benzo[1,3]dioxole;
2-methyl-1-oxo-2,8-diaza-spiro[4,5]decane;
2-oxa-5-aza-bicyclo [2.2.1]heptane; and
1-oxa-8-aza-spiro[4.5]decane;
R' and R" are independently from each other selected from lower alkyl, —(CH$_2$)$_n$—O-lower alkyl, cycloalkyl and cycloalkyl substituted by hydroxy;
n is 0, 1 or 2;

or pharmaceutically acceptable salts thereof.

In another embodiment, this invention relates to compounds of formula I wherein,
R$^1$ is phenyl;
R$^2$ is selected from
—(CH$_2$)$_n$-aryl;
—(CH$_2$)$_n$-aryl substituted by halogen;
heteroaryl substituted by one or more substituents selected from the group consisting of lower alkyl, lower alkoxy and —(CH$_2$)$_n$-heterocyclyl; and
—(CH$_2$)$_n$-cycloalkyl; and
n is 0, 1 or 2;

or pharmaceutically acceptable salts thereof.

In yet another embodiment, this invention relates to compounds of formula I wherein,
R$^1$ is tetrahydropyran-4-yl;
R$^2$ is selected from
—(CH$_2$)$_n$-aryl;
—(CH$_2$)$_n$-aryl substituted by halogen;

heteroaryl substituted lower alkyl, lower alkoxy and
—(CH$_2$)$_n$-heterocyclyl; and —(CH$_2$)$_n$-cycloalkyl; and
n is 0, 1 or 2;

or pharmaceutically acceptable salts thereof.

Preferred compounds of the present application are compounds of formula I, wherein R$^1$ is morpholinyl and R$^2$ is phenyl, unsubstituted or substituted by halogen, lower alkoxy or morpholinyl, for example the following compounds:
4-fluoro-N-(7-methoxy-4-morpholin-4-yl-thiazolo[5,4-c]pyridin-2-yl)-benzamide,
N-(7-methoxy-4-morpholin-4-yl-thiazolo[5,4-c]pyridin-2-yl)-benzamide,
4-methoxy-N-(7-methoxy-4-morpholin-4-yl-thiazolo[5,4-c]pyridin-2-yl)-benzamide,
3-fluoro-N-(7-methoxy-4-morpholin-4-yl-thiazolo[5,4-c]pyridin-2-yl)-benzamide,
3-methoxy-N-(7-methoxy-4-morpholin-4-yl-thiazolo[5,4-c]pyridin-2-yl)-benzamide,
3-methoxy-N-(7-methoxy-4-morpholin-4-yl-thiazolo[5,4-c]pyridin-2-yl)-4-methylbenzamide, or
N-(7-methoxy-4-morpholin-4-yl-thiazolo[5,4-c]pyridin-2-yl)-3-morpholin-4-yl-benzamide.

Further preferred are compounds, wherein R$^1$ is phenyl and R$^2$ is phenyl, unsubstituted or substituted by halogen or lower alkoxy, for example, the following compounds:
N-(7-methoxy-4-phenyl-thiazolo[5,4-c]pyridin-2-yl)-benzamide,
4-fluoro-N-(7-methoxy-4-phenyl-thiazolo[5,4-c]pyridin-2-yl)-benzamide, or
3-methoxy-N-(7-methoxy-4-phenyl-thiazolo[5,4-c]pyridin-2-yl)-benzamide.

Preferred compounds of the present application are compounds of formula I, wherein R$^1$ is morpholinyl and R$^2$ is —(CH$_2$)$_n$-cycloalkyl and n is 0 or 1, for example the following compounds:
2-cyclohexyl-N-(7-methoxy-4-morpholin-4-yl-thiazolo[5,4-c]pyridin-2-yl)-acetamide, or
cyclohexanecarboxylic acid (7-methoxy-4-morpholin-4-yl-thiazolo[5,4-c]pyridin-2-yl)-amide.

Further preferred are compounds, wherein R$^1$ is morpholinyl and R$^2$ is pyridyl, unsubstituted or substituted by one or more substituents, selected from the group consisting of —(CH$_2$)$_n$-heterocyclyl, which is optionally substituted by hydroxy or lower alkoxy, for example the following compounds:
2-(3-hydroxy-azetidin-1-yl)-N-(7-methoxy-4-morpholin-4-yl-thiazolo[5,4-c]pyridin-2-yl)-isonicotinamide,
2-(3-methoxy-azetidin-1-yl)-N-(7-methoxy-4-morpholin-4-yl-thiazolo[5,4-c]pyridin-2-yl)-isonicotinamide, or
N-(7-methoxy-4-morpholin-4-yl-thiazolo[5,4-c]pyridin-2-yl)-2-morpholin-4-yl-isonicotinamide.

Further preferred are compounds, wherein R$^1$ is phenyl and R$^2$ is pyridyl, unsubstituted or substituted by one or more substituents, selected from the group consisting of morpholinyl or lower alkyl, for example the following compounds:
N-(7-methoxy-4-phenyl-thiazolo[5,4-c]pyridin-2-yl)-2-morpholin-4-yl-isonicotinamide or
N-(7-methoxy-4-phenyl-thiazolo[5,4-c]pyridin-2-yl)-2-methyl-isonicotinamide.

Further preferred are compounds, wherein R$^1$ is morpholinyl and R$^2$ is benzo[1,3]dioxole or 2-oxa-5-aza-bicyclo [2.2.1]heptane, for example the following compounds:
benzo[1,3]dioxole-5-carboxylic acid (7-methoxy-4-morpholin-4-yl-thiazolo[5,4-c]pyridin-2-yl)-amide or
(1S,4S)-2-oxa-5-aza-bicyclo[2.2.1]heptane-5-carboxylic acid (7-methoxy-4-morpholin-4-yl-thiazolo[5,4-c]pyridin-2-yl)-amide.

The present compounds of formula I and their pharmaceutically acceptable salts can be prepared by methods known in the art, for example, by processes described below, which process comprises reacting a compound of formula

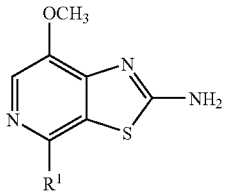
(7)

with a compound of formula

ClC(O)R²/base (20)

to form the compound of formula

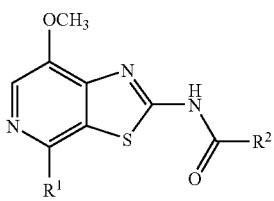
I wherein R¹ and R² are as defined above, and if desired, converting the compound obtained into its pharmaceutically acceptable salt.

In another aspect of this invention, the present compounds of formula I and their pharmaceutically acceptable salts can be prepared by methods known in the art, for example, by processes described below, which process comprises reacting a compound of formula

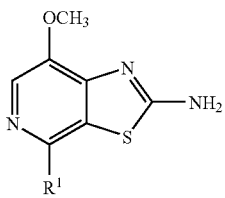
(7)

with a compound of formula

HOC(O)R²/HATU/base (21)

to form a compound of formula

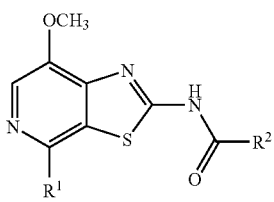
I wherein R¹ and R² are as defined above, and if desired, converting the compound obtained into its pharmaceutically acceptable salt.

In another aspect of this invention, the present compounds of formula I and their pharmaceutically acceptable salts can be prepared by methods known in the art, for example, by processes described below, which process comprises reacting a compound of formula

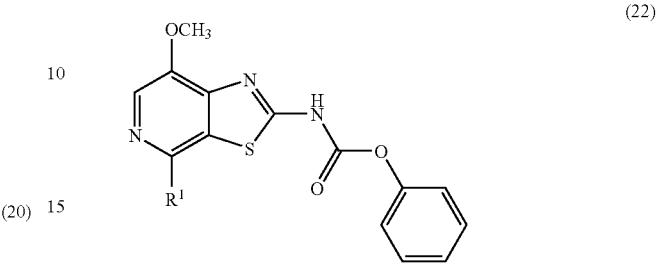
(22)

with a compound of formula

HR²/base (23)

to form a compound of formula

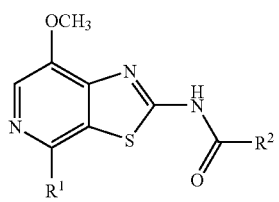
I wherein R¹ is as defined above and R² is piperidine-1-yl, optionally substituted by one or more substituents selected from the group consisting of —(CH₂)ₙ—OH, —(CH₂)ₙ—O-lower alkyl or lower alkyl, or is morpholinyl, or is NR'R", or is 2-methyl-1-oxo-2,8-diaza-spiro[4,5]decane, 2-oxa-5-aza-bicyclo[2.2.1]heptane or 1-oxa-8-aza-spiro[4.5]decane, and R', R" are independently from each other lower alkyl, —(CH₂)ₙ—O-lower alkyl or cycloalkyl, optionally substituted by hydroxy and n is 0-2, and if desired, converting the compound obtained into its pharmaceutically acceptable salt.

In an aspect of this invention, the present compounds of formula Ia and their pharmaceutically acceptable salts can be prepared by methods known in the art, for example, by processes described below, which process comprises reacting a compound of formula

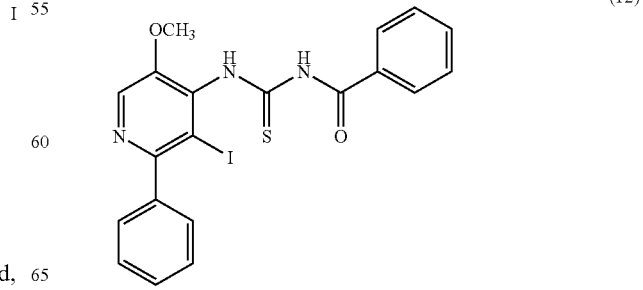
(12)

with CuI (cat), phenanthroline (cat) in the presence of Cs₂CO₃ to form a compound of formula

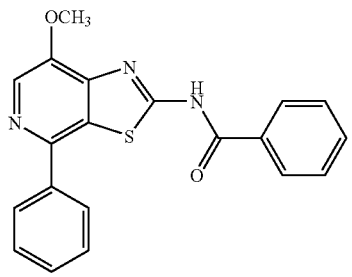

Ia and if desired, converting the compound obtained into its pharmaceutically acceptable salt.

In an aspect of this invention, the present compounds of formula Ia and their pharmaceutically acceptable salts can be prepared by methods known in the art, for example, by processes described below, which process comprises reacting a compound of formula Ib

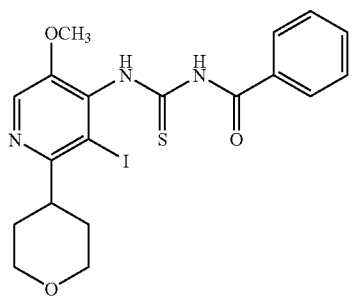

(19)

with CuI (cat), phenanthroline (cat) in the presence of Cs₂CO₃ to a compound of formula

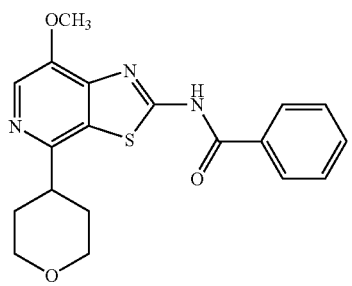

Ib and if desired, converting the compound obtained into its pharmaceutically acceptable salt.

The compounds of formula I may be prepared in accordance with process variants a)-e) and with the following schemes 1-5.

Preparation of Compounds of Formula I

Compounds of formula I may be prepared from intermediate compounds of formula (7) as shown in reaction schemes 4 and 5. The intermediate compounds of formula (7) may be prepared as shown in reaction schemes 1, 2 and 3 below.

Preparation of an Intermediate Compound of Formula (7) wherein R¹ is morpholin-4-yl The preparation of an intermediate compound of formula (7) wherein R¹ is morpholin-4-yl is shown in reaction scheme 1 below.

Scheme 1

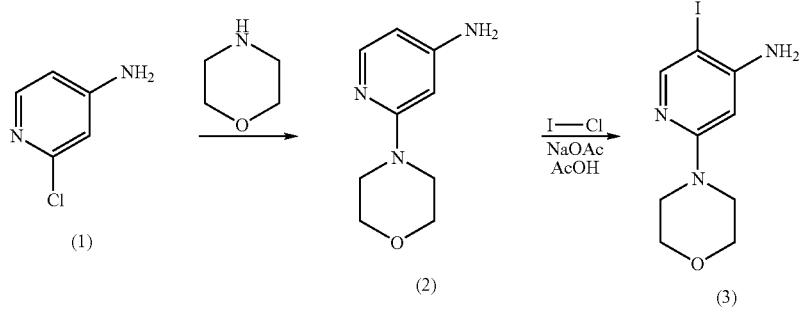

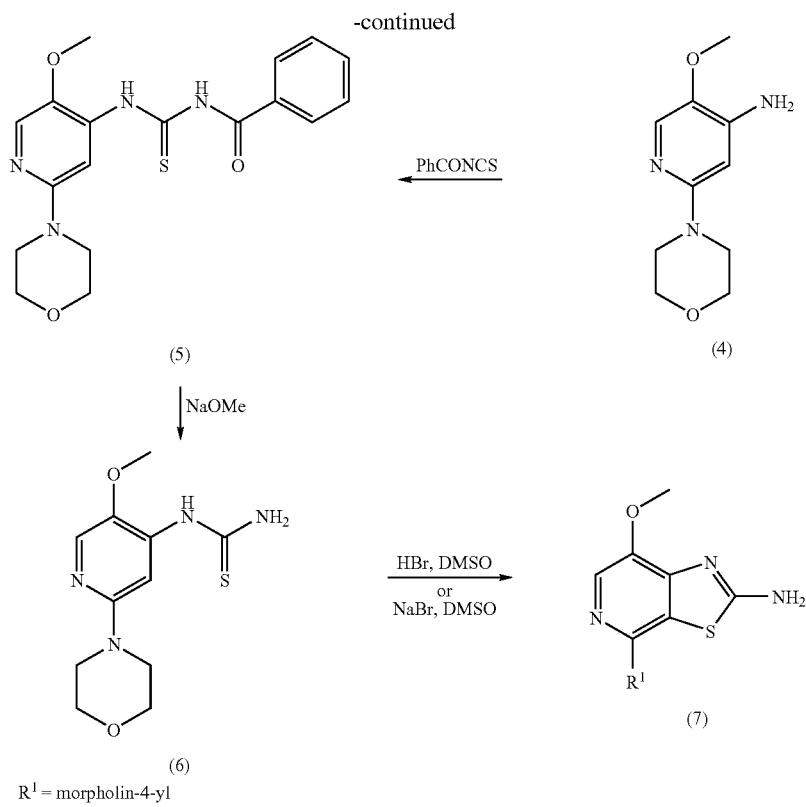

(5)

(4)

(6)
R¹ = morpholin-4-yl (7)

Preparation of Intermediate Compound of Formula (2)

The starting compound of formula (1), 4-amino-2-chloropyridine, may be obtained commercially, for example from Acros, or may be prepared according to methods well known in the art.

The chloropyridine compound of formula (1) is reacted with an excess of morpholine at elevated temperature. The reaction is preferably carried out in a suitably equipped microwave oven, preferably at about 200° C. for about 30 minutes. The product of formula (2) is isolated by conventional means, and preferably purified by means of chromatography or recrystallization.

Preparation of Intermediate Compound of Formula (3)

The intermediate of formula (2) is reacted with a slight excess of an iodinating reagent, preferably iodine monochloride, in an organic solvent, preferably acetic acid. The reaction is carried out in the presence of a weak base, preferably sodium acetate, at room temperature or just below, preferably at around 10-15° C., for about 1 hour. The product of formula (3) is isolated by conventional means, and preferably purified by means of chromatography or recrystallization.

Preparation of Intermediate Compound of Formula (4)

The intermediate of formula (3) is reacted with methanol, which is preferably used as solvent for the reaction, in the presence of a metal catalyst, preferably copper(I) iodide, and a catalytic amount of an amine ligand, preferably 1,10-phenanthroline, according to a modification of the procedure of Buchwald et al. (*Org. Letters*. 2002, 4, 973). The reaction is carried out in the presence of a base, preferably cesium carbonate. The reaction is carried out at elevated temperature, preferably in a suitably equipped microwave oven, preferably at about 130° C. for about 30 minutes. The product of formula (4) is isolated by conventional means, and preferably purified by means of chromatography or recrystallization.

Preparation of Intermediate Compound of Formula (5)

The intermediate of formula (4) is reacted with benzoyl isothiocyanate in acetone. The reaction is carried out at room temperature or above, preferably at the reflux temperature of the solvent, for about 1-2 hours. The product of formula (5) is isolated by conventional means, and preferably purified by means of chromatography or recrystallization.

Preparation of Intermediate Compound of Formula (6)

The intermediate of formula (5) is treated with a substoichiometric amount of an alkali metal alcoholate in the corresponding alcohol solvent, preferably sodium methylate in methanol. The reaction is carried out at room temperature or above, preferably at around 60° C., for about 0.5-2 hours. The product of formula (6) is isolated by conventional means, and preferably purified by means of chromatography or recrystallization.

Preparation of Intermediate Compound of Formula (7) wherein R¹ is morpholin-4-yl One method of preparation of an intermediate compound of Formula (7) wherein R¹ is morpholin-4-yl is by treatment of a compound of formula (6) with a slight excess of hydrobromic acid in an organic solvent, such as ethyl acetate or acetic acid, preferably a mixture of ethyl acetate and acetic acid. The reaction is carried out at elevated temperature, preferably about 80° C., for about 15-60 minutes, preferably about 15 minutes. This mixture is then treated with DMSO at elevated temperature, preferably about 80°

C., for about 5 to 30 minutes, preferably about 30 minutes. The product of formula (7) is isolated by conventional means, and preferably purified by means of chromatography or recrystallization. In an alternative method, a compound of formula (7) is treated with a catalytic amount of sodium bromide in concentrated sulfuric acid at elevated temperature, preferably at about 75° C., for about 1-2 hours. The product of formula (7) is isolated by conventional means, and preferably purified by means of chromatography or recrystallization.

Preparation of an Intermediate Compound of Formula (7) Wherein $R^1$ is Phenyl

The preparation of an intermediate compound of formula (7) wherein $R^1$ is phenyl is shown in reaction scheme 2 below.

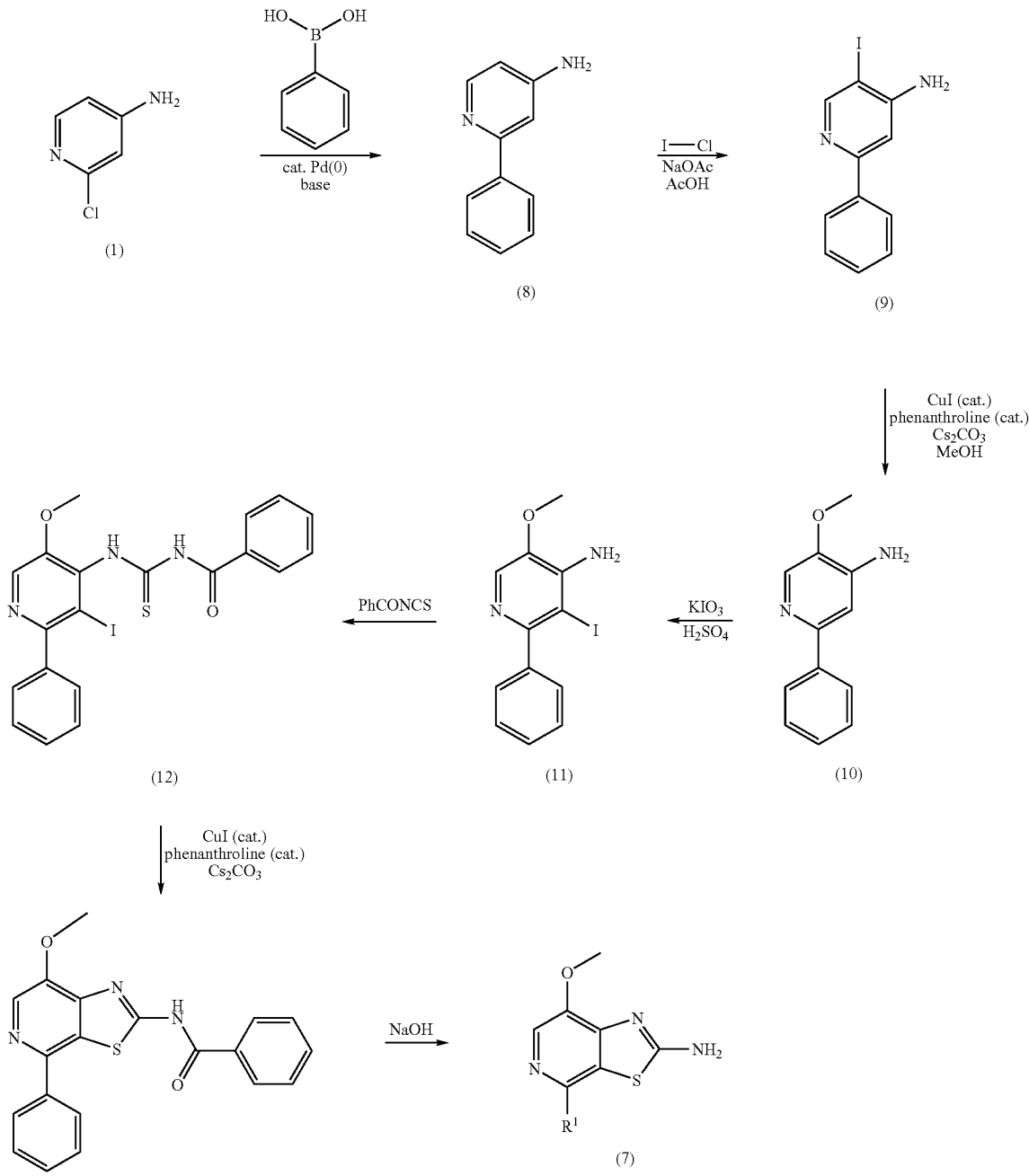

Preparation of Intermediate Compound of Formula (8)

The starting compound of formula (1), 4-amino-2-chloropyridine, may be obtained commercially, for example from Acros, or may be prepared according to methods well known in the art.

The chloropyridine compound of formula (1) is reacted with an excess of phenylboronic acid. The reaction is carried out in an aqueous solvent system, preferably a mixture of water and toluene, containing a palladium catalyst, preferably tetrakis(triphenylphosphine)palladium(0), and an inorganic base, preferably sodium carbonate. The reaction is preferably carried out at the reflux temperature of the solvent, preferably about 100° C., for about 2-24 hours, preferably about 16 hours. The product of formula (8) is isolated by conventional means, and preferably purified by means of chromatography or recrystallization.

Preparation of Intermediate Compound of Formula (9)

The intermediate of formula (8) is reacted with a slight excess of an iodinating reagent, preferably iodine monochloride, in an organic solvent, preferably acetic acid. The reaction is carried out in the presence of a weak base, preferably sodium acetate, at room temperature for about 1-48 hours. The product of formula (9) is isolated by conventional means, and preferably purified by means of chromatography or recrystallization.

Preparation of Intermediate Compound of Formula (10)

The intermediate of formula (9) is reacted with methanol, which is preferably used as solvent for the reaction, in the presence of a metal catalyst, preferably copper(I) iodide, and a catalytic amount of an amine ligand, preferably 1,10-phenanthroline, according to a modification of the procedure of Buchwald et al. (*Org. Letters.* 2002, 4, 973). The reaction is carried out in the presence of a base, preferably cesium carbonate. The reaction is carried out at elevated temperature, preferably in a suitably equipped microwave oven, preferably at about 130° C. for about 20 minutes. The product of formula (10) is isolated by conventional means, and preferably purified by means of chromatography or recrystallization.

Preparation of Intermediate Compound of Formula (11)

The intermediate of formula (10) is reacted with an excess of an iodinating reagent, preferably potassium iodate, in an acidic solvent, preferably concentrated sulfuric acid. The reaction is carried out at elevated temperature, preferably at 100° C., for about 1-12 hours. The product of formula (11) is isolated by conventional means, and preferably purified by means of chromatography or recrystallization.

Preparation of Intermediate Compound of Formula 12

The intermediate of formula (11) is reacted with benzoyl isothiocyanate in acetone. The reaction is carried out at room temperature or above, preferably at the reflux temperature of the solvent, for about 1-5 hours. The product of formula (12) is isolated by conventional means, and preferably purified by means of chromatography or recrystallization.

Preparation of a Compound of Formula Ia

The intermediate of formula (12) is reacted in the presence of a metal catalyst, preferably copper(I) iodide, and a catalytic amount of an amine ligand, preferably 1,10-phenanthroline. The reaction is carried out in the presence of a base, preferably cesium carbonate. The reaction is carried out in an organic solvent, preferably toluene, at elevated temperature, preferably in a suitably equipped microwave oven, preferably at about 130° C. for about 5-10 minutes. The product of formula Ia is isolated by conventional means, and preferably purified by means of chromatography or recrystallization. The reaction may also be carried out in the presence of the base alone, omitting the copper catalyst and amine ligand, but in this case lower yields of product of formula Ia are obtained.

Preparation of Intermediate Compound of Formula (7) Wherein $R^1$ is Phenyl

The compound of formula Ia may be converted to the corresponding intermediate of formula (7) by reaction with an excess of an aqueous base such as lithium hydroxide, sodium hydroxide or potassium hydroxide, preferably sodium hydroxide. The reaction is carried out in an aqueous solvent, preferably a mixture of water and a miscible organic solvent such as dioxane, tetrahydrofuran or methanol, preferably methanol, at an elevated temperature, preferably in a suitably equipped microwave oven, preferably at about 130° C. for about 10 minutes. The product of formula (7) is isolated by conventional means, and preferably purified by means of chromatography or recrystallization.

Preparation of an Intermediate Compound of Formula (7) Wherein $R^1$ is tetrahydropyran-4-yl The preparation of an intermediate compound of formula (7) wherein $R^1$ is tetrahydropyran-4-yl is shown in reaction scheme 3 below.

Scheme 3

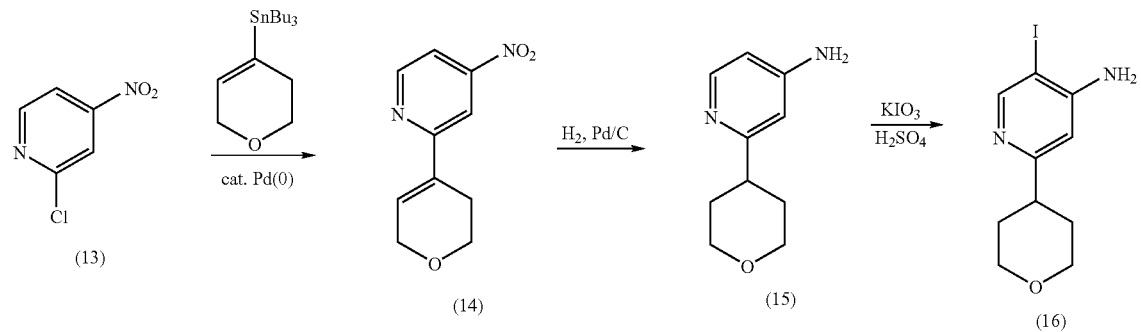

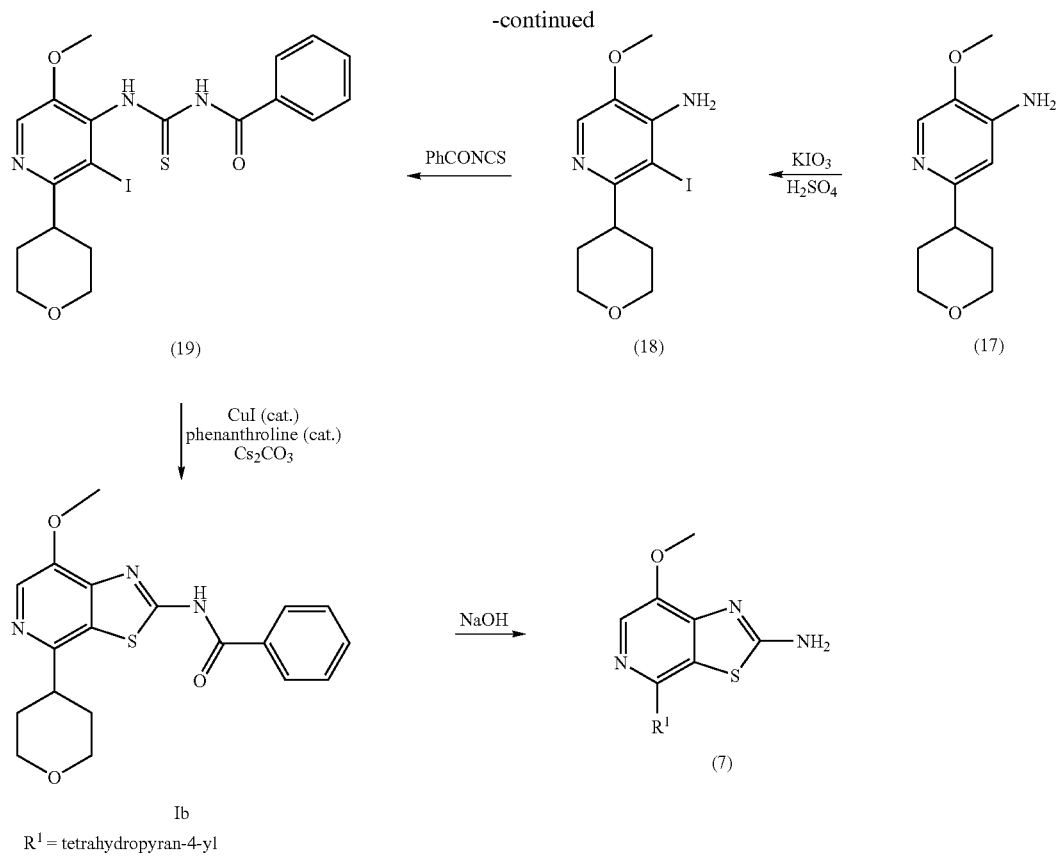

Ib
R¹ = tetrahydropyran-4-yl

Preparation of Intermediate Compound of Formula (14)

The starting compound of formula (13), 2-chloro-4-nitropyridine, may be obtained commercially, for example from Lancaster, or may be prepared according to methods well known in the art. Tributyl-(3,6-dihydro-2H-pyran-4-yl)-stannane may be prepared according to methods well known in the art.

The chloropyridine compound of formula (13) is reacted with an excess of tributyl(3,6-dihydro-2H-pyran-4-yl)-stannane. The reaction is carried out in an organic solvent, preferably N,N-dimethylformamide, containing a palladium catalyst, preferably bis(triphenylphosphine)palladium(II) chloride, and other additives such as excess triphenylphosphine, lithium chloride and 2,6-di-tert-butyl-p-cresol. The reaction is carried out at elevated temperature, preferably about 100° C., for about 2-16 hours, preferably about 4 hours. The product of formula (14) is isolated by conventional means, and preferably purified by means of chromatography or recrystallization.

Preparation of Intermediate Compound of Formula (15)

The intermediate of formula (15) may be prepared by hydrogenation of the intermediate of formula (14) in the presence of a hydrogenation catalyst, preferably 10% palladium on charcoal. The reaction may be carried out in a variety of organic solvents, preferably a mixture of tetrahydrofuran and acetic acid, at room temperature and at a pressure of one atmosphere or above, preferably at 1.7 bar, for 16-24 hours, preferably about 16 hours. The product of formula (15) is isolated by conventional means, and preferably purified by means of chromatography or recrystallization.

Preparation of Intermediate Compound of Formula (16)

The intermediate of formula (15) is reacted with a slight excess of an iodinating reagent, preferably potassium iodate, in an acidic solvent, preferably 65% aqueous sulfuric acid. The reaction is carried out at elevated temperature, preferably at 135° C., for about 1-3 hours. The product of formula (16) is isolated by conventional means, and preferably purified by means of chromatography or recrystallization.

Preparation of Intermediate Compound of Formula (17)

The intermediate of formula (16) is reacted with methanol, which is preferably used as solvent for the reaction, in the presence of a metal catalyst, preferably copper(I) iodide, and a catalytic amount of an amine ligand, preferably 1,10-phenanthroline, according to a modification of the procedure of Buchwald et al. (*Org. Letters.* 2002, 4, 973). The reaction is carried out in the presence of a base, preferably cesium carbonate. The reaction is carried out at elevated temperature, preferably in a suitably equipped microwave oven, preferably at about 130° C. for about 5-10 minutes. The product of formula (17) is isolated by conventional means, and preferably purified by means of chromatography or recrystallization.

Preparation of Intermediate Compound of Formula (18)

The intermediate of formula (17) is reacted with an excess of an iodinating reagent, preferably potassium iodate, in an acidic solvent, preferably 65% aqueous sulfuric acid. The reaction is carried out at elevated temperature, preferably at 100° C., for about 1-3 hours. The product of formula (18) is isolated by conventional means, and preferably purified by means of chromatography or recrystallization.

Preparation of Intermediate Compound of Formula (19)

The intermediate of formula (18) is reacted with benzoyl isothiocyanate in acetone. The reaction is carried out at room temperature or above, preferably at the reflux temperature of the solvent, for about 1-5 hours. The product of formula (19) is isolated by conventional means, and preferably purified by means of chromatography or recrystallization.

Preparation of a Compound of Formula Ib

The intermediate of formula (19) is reacted in the presence of a metal catalyst, preferably copper(I) iodide, and a catalytic amount of an amine ligand, preferably 1,10-phenanthroline. The reaction is carried out in the presence of a base, preferably cesium carbonate. The reaction is carried out in an organic solvent, preferably toluene, at elevated temperature, preferably in a suitably equipped microwave oven, preferably at about 130° C. for about 5-10 minutes. The product of formula Ib is isolated by conventional means, and preferably purified by means of chromatography or recrystallization. The reaction may also be carried out in the presence of the base alone, omitting the copper catalyst and amine ligand, but in this case lower yields of product of formula Ib are obtained.

Preparation of Intermediate Compound of Formula (7) Wherein $R^1$ is tetrahydropyran-4-yl The compound of formula Ib may be converted to the corresponding intermediate of formula (7) by reaction with an excess of an aqueous base such as lithium hydroxide, sodium hydroxide or potassium hydroxide, preferably sodium hydroxide. The reaction is carried out in an aqueous solvent, preferably a mixture of water and a miscible organic solvent such as dioxane, tetrahydrofuran or methanol, preferably methanol, at an elevated temperature, preferably in a suitably equipped microwave oven, preferably at about 130° C. for about 10 minutes. The product of formula (7) is isolated by conventional means, and preferably purified by means of chromatography or recrystallization.

Preparation of Compounds of Formula I

Compounds of formula I may be prepared from compounds of formula (7), as shown in reaction scheme 4 below.

HATU is O-(7-azabenzotriazol-1-yl)-N,N,N',N'-tetramethyluranium hexafluorophosphate.

Preparation of Compounds of Formula I

One method of preparation of compounds of formula I is by treatment of a compound of formula (7) with a slight excess of an appropriate acyl chloride of formula (20), which may be commercially available or may be prepared by methods well known in the art. The reaction is carried out in a non-protic organic solvent, preferably a mixture of dichloroethane and tetrahydrofuran, containing a base, preferably N-ethyldiisopropylamine, at room temperature or above, preferably at around 80° C., for 1-2 hours. The product of formula I is isolated by conventional means, and preferably purified by means of chromatography or recrystallization.

Alternative Preparation of Compounds of Formula I

An alternative method of preparation of compounds of formula I involves treatment of an appropriate carboxylic acid of formula (21) with a stoichiometric equivalent of a peptide-coupling reagent, preferably O-(7-azabenzotriazol-1-yl)-N,N,N',N'-tetramethyluronium hexafluorophosphate (HATU), in an ethereal solvent, preferably tetrahydrofuran, containing a base, preferably N-methylmorpholine, at room temperature or above, preferably at around 30° C., for 1-16 hours, preferably 16 hours. This mixture is then treated with a compound of formula (7) at room temperature or above, preferably at around 30-50° C., for 16-48 hours, preferably 16 hours. The product of Formula I is isolated by conventional means, and preferably purified by means of chromatography or recrystallization.

Alternative Preparation of Compounds of Formula I

An alternative method of preparation of compounds of formula I from compounds of formula (7) is via intermediate compounds of formula (22), the preparation of which is shown in reaction scheme 5 below.

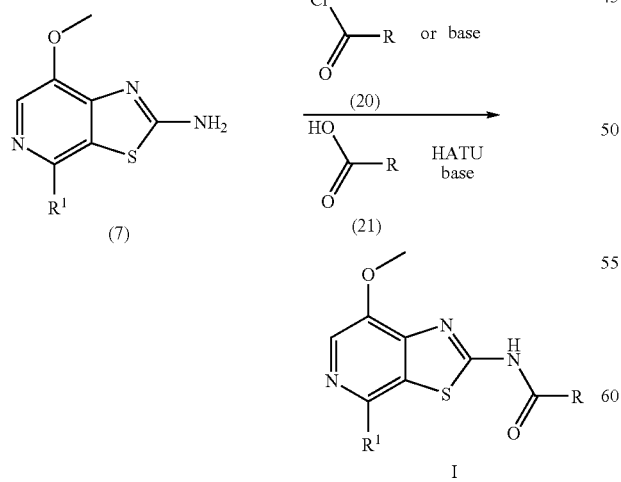

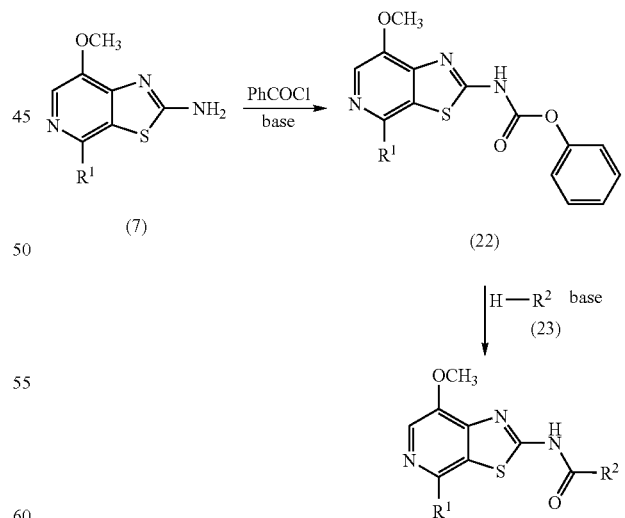

wherein $R^1$ and $R^2$ are as defined above, with the exception of cases where $R^2$ is attached by an atom other than C, and wherein $R^1$ is as defined above, $R^2$ is piperidine-1-yl, optionally substituted by one or more substituents selected from the group consisting of —$(CH_2)_n$—OH, —$(CH_2)_n$—O-lower alkyl or lower alkyl, or is morpholinyl, or is NR'R", or is 2-methyl-1-oxo-2,8-diaza-spiro[4,5]decane, 2-oxa-5-aza-bicyclo[2.2.1]heptane or 1-oxa-8-aza-spiro[4.5]decane, and R', R" are independently from each other lower alkyl, —$(CH_2)_n$—O-lower alkyl or cycloalkyl, optionally substituted by hydroxy and n is 0-2;

Preparation of Compounds of Formula (22)

One method of preparation of the compounds of formula (22) is by treatment of a compound of formula (7) with a slight excess of phenyl chloroformate in a non-protic organic solvent, preferably a mixture of dichloromethane and tetrahydrofuran, in the presence of a base, preferably pyridine. The reaction is carried out at room temperature or above, preferably at around 50° C., for about 1-16 hours, preferably about 3 hours. The product of formula (22) is isolated by conventional means, and preferably purified by means of chromatography or recrystallization.

Preparation of Compounds of Formula I

One method of preparation of compounds of formula I is by treatment of the compounds of formula (22) with an excess of an appropriate amine of formula (23), which may be commercially available or may be prepared by methods well known in the art. The reaction is carried out in an aprotic organic solvent, preferably a mixture of dichloroethane and tetrahydrofuran, containing a base, preferably N-ethyldiisopropylamine or pyridine or the amine (23) itself, at an elevated temperature, preferably around 50° C., for 2-24 hours, preferably 16 hours. The product of formula I is isolated by conventional means, and preferably purified by means of chromatography or recrystallization.

Conversion of Compounds of Formula I to Other Compounds of Formula I Bearing a Modified $R^2$ Substituent In cases where the compound of formula I contains an $R^2$ substituent bearing a chemically reactive functional group, for instance when $R^2$ contains benzylic halide functionality or 2-halo-pyridyl functionality, the compound of formula I may be converted to another compound of formula I having a modified $R^2$ substituent, by reactions involving the reactive functionality contained in the original $R^2$ substituent. Such transformations may be carried out according to methods well known in the art and specific examples may be obtained from a number of the examples provided below. For instance, compounds of formula I containing $R^2$ substituents bearing benzylic halide functionality or 2-halo-pyridyl functionality may be reacted with nucleophilic alcohol or amine reagents to afford compounds of formula I containing $R^2$ substituents bearing, respectively, benzylic ether or benzylic amine functional groups, or pyridyl-2-yl-ether or pyridyl-2-yl-amino functional groups.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be obtained by reference to the Preparations and Examples herein below. However, other equivalent separation or isolation procedures could, of course, also be used.

Salts of Compounds of formula I

The compounds of formula I may be basic, for example in cases where the residue $R^2$ contains a basic group such as an aliphatic or aromatic amine moiety. In such cases the compounds of formula I may be converted to a corresponding acid addition salt.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluene sulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention are adenosine receptor ligands and possess a high affinity towards the adenosine $A_{2A}$ receptor and a good selectivity towards $A_1$ and $A_3$ receptors. The compounds were investigated in accordance with the tests given hereinafter.

Human Adenosine $A_1$ Receptor

The human adenosine $A_1$ receptor was recombinantly expressed in Chinese hamster ovary (CHO) cells using the semliki forest virus expression system. Cells were harvested, washed twice by centrifugation, homogenized and again washed by centrifugation. The [$^3$H]-DPCPX (([propyl-3H] 8-cyclopentyl-1,3-dipropyxanthine); 0.6 nM) binding assay was carried out in 96-well plates in the presence of (per well) approximately 2.5 µg of membrane protein, 0.5 mg of Ysi-poly-1-lysine SPA beads and 0.1 U adenosine deaminase in a final volume of 200 µl of buffer (containing 50 mM Tris, 120 mM NaCl, 5 mM KCl, 2 mM $CaCl_2$ and 10 mM $MgCl_2$ (pH 7.4)). Non-specific binding was defined using xanthine amine congener (XAC; 2 µM). Compounds were tested at 10 concentrations from 10 µM-0.3 nM. All assays were conducted in duplicate and repeated at least two times. Assay plates were incubated for 1 hour at room temperature before centrifugation and then bound ligand determined using a Packard Topcount scintillation counter. $IC_{50}$ values were calculated using a non-linear curve fitting program and $K_i$ values calculated using the Cheng-Prussoff equation.

Human Adenosine $A_{2A}$ Receptor

The human adenosine $A_{2A}$ receptor was recombinantly expressed in Chinese hamster ovary (CHO) cells using the semliki forest virus expression system. Cells were harvested, washed twice by centrifugation, homogenized and again washed by centrifugation. The [$^3$H]-SCH-58261 (Dionisotti et al., 1997, Br J Pharmacol 121, 353; 1 nM) binding assay was carried out in 96-well plates in the presence of (per well) approximately 2.5 µg of membrane protein, 0.5 mg of Ysi-poly-1-lysine SPA beads and 0.1 U adenosine deaminase in a final volume of 200 µl of buffer (containing 50 mM Tris, 120 mM NaCl, 5 mM KCl, 2 mM CaCl$_2$ and 10 mM MgCl$_2$ (pH 7.4)). Non-specific binding was defined using xanthine amine congener (XAC; 2 µM). Compounds were tested at 10 concentrations from 10 µM-0.3 nM. All assays were conducted in duplicate and repeated at least two times. Assay plates were incubated for 1 hour at room temperature before centrifugation and then bound ligand determined using a Packard Topcount scintillation counter. IC$_{50}$ values were calculated using a non-linear curve fitting program and K$_i$ values calculated using the Cheng-Prussoff equation.

It has been shown that compounds of formula I have a good affinity to the A$_{2A}$ receptor and a high selectivity toward the A$_1$ and A$_3$ receptor. The hA$_{2A}$ pKi of the present compounds is in the range of 7.19-8.51. The preferred compounds show a hA$_{2A}$ pKi>8.00.

| Example No. | hA$_1$ | hA$_{2A}$ | Selectivity |
|---|---|---|---|
| 1 | 5.75 | 8.38 | 420 |
| 3 | 5.72 | 8.30 | 384 |
| 4 | 5.24 | 7.95 | 512 |
| 5 | 5.20 | 7.89 | 489 |
| 6 | 5.78 | 8.27 | 312 |
| 7 | 5.87 | 8.51 | 436 |
| 8 | 5.14 | 7.86 | 535 |
| 9 | 5.42 | 8.14 | 527 |
| 11 | 5.30 | 7.79 | 310 |
| 17 | 5.25 | 7.66 | 258 |
| 18 | 516 | 8.10 | 868 |
| 19 | 5.72 | 8.26 | 347 |
| 21 | 5.14 | 7.85 | 519 |
| 22 | 5.19 | 8.41 | 1647 |
| 29 | 5.14 | 7.90 | 572 |
| 30 | 5.15 | 8.39 | 1716 |
| 31 | 5.22 | 7.86 | 441 |
| 33 | 5.14 | 7.60 | 291 |
| 36 | 5.50 | 8.17 | 468 |
| 37 | 5.14 | 7.68 | 346 |
| 39 | 5.14 | 7.79 | 446 |
| 40 | 5.23 | 7.81 | 387 |
| 43 | 5.15 | 7.93 | 593 |

The compounds of formula I and the pharmaceutically acceptable salts of the compounds of formula I can be used as medicaments, e.g. in the form of pharmaceutical preparations or pharmaceutical compositions. The pharmaceutical compositions can be administered orally, e.g. in the form of tablets, coated tablets, dragées, hard and soft gelatine capsules, solutions, emulsions or suspensions. The administration can, however, also be effected rectally, e.g. in the form of suppositories, parenterally, e.g. in the form of injection solutions.

The compounds of formula I can be processed with pharmaceutically inert, inorganic or organic carriers for the production of pharmaceutical compositions. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semisolid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Pharmaceutical compositions containing a compound of formula I or a pharmaceutically acceptable salt thereof and a therapeutically inert carrier are also related to the present invention, as is a process for their production, which comprises bringing one or more compounds of formula I and/or pharmaceutically acceptable salts and, if desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the adenosine receptor antagonistic activity, such as Alzheimer's disease, Parkinson's disease, neuroprotection, schizophrenia, anxiety, pain, respiration deficits, depression, asthma, allergic responses, hypoxia, ischaemia, seizure and substance abuse. Furthermore, compounds of the present invention may be useful as sedatives, muscle relaxants, antipsychotics, antiepileptics, anticonvulsants and cardiaprotective agents and for the production of corresponding medicaments.

The most preferred indications in accordance with the present invention are those, which include disorders of the central nervous system, for example the treatment or prevention of certain depressive disorders, neuroprotection and Parkinson's disease.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

| Item | Ingredients | Tablet Formulation (Wet Granulation) mg/tablet | | | |
|---|---|---|---|---|---|
| | | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Item | Ingredients | Capsule Formulation mg/capsule | | | |
|---|---|---|---|---|---|
| | | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |

| | | | | |
|---|---|---|---|---|
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

EXAMPLES

The following preparation and examples illustrate the invention but are not intended to limit its scope.

Example 1

4-Fluoro-N-(7-methoxy-4-morpholin-4-yl-thiazolo[5,4-c]pyridin-2-yl)-benzamide a) 2-Morpholin-4-yl-pyridin-4-ylamine A stirred mixture of 45.8 g (356 mmol) 4-amino-2-chloropyridine in 124 ml morpholine was heated at 200° C. for 30 min in a microwave oven. The resulting yellow solution was then cooled to room temperature whereupon crystals appeared. 400 ml ether was then added and the suspension stirred for 10 minutes before being filtered. The filter cake was washed with ether and dried to afford 92.9 g of crystalline material (87% yield of desired product) which $^1$H NMR analysis revealed to comprise 60 wt % 2-morpholin-4-yl-pyridin-4-ylamine and 40 wt % morpholine. This material was used in the next step without any further purification. ES-MS m/e (%): 180 (M+H$^+$, 100).

b) 5-Iodo-2-morpholin-4-yl-pyridin-4-ylamine

To a stirred solution of 92.8 g (311 mmol, 60 wt % purity) 2-morpholin-4-yl-pyridin-4-ylamine in 1000 ml glacial acetic acid was added 76.5 g (932 mmol) sodium acetate and the mixture was then cooled to 15° C. in an ice-bath. A solution of 50.4 g (311 mmol) iodine monochloride in 200 ml glacial acetic acid was then added dropwise at a rate such that the reaction temperature remained at 10-15° C. After 40 min the addition was complete. The reaction mixture was then stirred for a further 20 min before being poured onto 1000 ml water. The mixture was concentrated in vacuo and the residue partitioned between THF/ethyl acetate (1:1) and saturated brine. 5 N aqueous sodium hydroxide solution was added until the aqueous phase was pH 14, whereupon some product precipitated. The crystals were collected by filtration to afford 16.9 g (18%) 5-iodo-2-morpholin-4-yl-pyridin-4-ylamine as a yellow crystalline solid. The mother liquid phases were separated and the organic phase dried over sodium sulfate and concentrated in vacuo. The residue was triturated in ether and the resulting crystals collected by filtration to afford a further 47.2 g (50%) of 5-iodo-2-morpholin-4-yl-pyridin-4-ylamine as a yellow crystalline solid. The mother liquor was concentrated in vacuo and the residue was purified by flash chromatography (1/1-1/2 heptane/ethyl acetate) to afford a further 9.4 g (10%) 5-iodo-2-morpholin-4-yl-pyridin-4-ylamine as a yellow crystalline solid. Meanwhile, the aqueous phase from the initial aqueous extraction was left to stand for 2 days whereupon crystals deposited. These crystals were collected by filtration to afford a further 5.2 g (5%) 5-iodo-2-morpholin-4-yl-pyridin-4-ylamine as a yellow crystalline solid. ES-MS m/e (%): 306 (M+H$^+$, 100).

c) 5-Methoxy-2-morpholin-4-yl-pyridin-4-ylamine

A stirred suspension of 81.4 g (267 mmol) 5-iodo-2-morpholin-4-yl-pyridin-4-ylamine, 4.06 g (21.3 mmol) copper(I) iodide, 5.77 g (32.0 mmol) 1,10-phenanthroline and 174 g (533 mmol) cesium carbonate in 600 ml methanol was heated at 130° C. for 30 min in a microwave oven. The resulting mixture was then cooled to room temperature and filtered. The filtrate was concentrated in vacuo and the residue purified by flash chromatography (1/7 methanol/dichloromethane) to afford 27.7 g (50%) 5-methoxy-2-morpholin-4-yl-pyridin-4-ylamine as a dark brown crystalline solid. ES-MS m/e (%): 210 (M+H$^+$, 100).

d) 1-Benzoyl-3-(5-methoxy-2-morpholin-4-yl-pyridin-4-yl)-thiourea

To a stirred solution of 27.5 g (132 mmol) 5-methoxy-2-morpholin-4-yl-pyridin-4-ylamine in 400 ml acetone was added dropwise 19.5 ml (145 mmol) benzoyl isothiocyanate at room temperature. The reaction mixture then heated at reflux for 90 min before being cooled to room temperature and poured onto 400 ml hexane and stirred for 5 min. The resulting crystals were collected by filtration, washed with hexane and dried to afford 32.5 g (66%) 1-benzoyl-3-(5-methoxy-2-morpholin-4-yl-pyridin-4-yl)-thiourea as a brown crystalline solid. ES-MS m/e (%): 373 (M+H$^+$, 100).

e) (5-Methoxy-2-morpholin-4-yl-pyridin-4-yl)-thiourea

To a stirred solution of 5.80 g (15.6 mmol) 1-benzoyl-3-(5-methoxy-2-morpholin-4-yl-pyridin-4-yl)-thiourea in 100 ml tetrahydrofuran and 25 ml methanol heated at 60° C. was added dropwise 1.15 ml (6.23 mmol) 5.4 M sodium methylate solution and stirring continued for 2 h at 60° C. 1.2 ml concentrated hydrochloric acid was then added and the reaction mixture concentrated in vacuo. The residue was triturated in 25 ml ether to afford 3.51 g (84%) (5-methoxy-2-morpholin-4-yl-pyridin-4-yl)-thiourea as alight brown crystalline solid. ES-MS m/e (%): 269 (M+H$^+$, 100).

f) 7-Methoxy-4-morpholin-4-yl-thiazolo[5,4-c]pyridin-2-ylamine

To a stirred suspension of 3.51 g (13.1 mmol) (5-methoxy-2-morpholin-4-yl-pyridin-4-yl)-thiourea in 75 ml ethyl acetate heated to reflux was added dropwise over 5 min 4.59 ml (26.2 mmol) hydrobromic acid (5.7 M solution in acetic acid) and stirring continued for a further 15 min. 1.12 ml (15.7 mmol) DMSO was then added dropwise and the reaction mixture stirred for a further 30 min at reflux. The mixture was then cooled to room temperature and partitioned between tetrahydrofuran and saturated brine. 5 N sodium hydroxide solution was added until the aqueous phase was pH 14, then 10% aq. citric acid solution was added until the aqueous phase was pH 6. The mixture was stirred for 20 min and then the phases were separated. The organic phase was dried over sodium sulfate and concentrated in vacuo. Trituration of the residue in ether afforded 2.23 g (64%) 7-methoxy-4-morpholin-4-yl-thiazolo[5,4-c]pyridin-2-ylamine as an off-white crystalline solid. ES-MS m/e (%): 267 (M+H$^+$, 100).

g) 4-Fluoro-N-(7-methoxy-4-morpholin-4-yl-thiazolo[5,4-c]pyridin-2-yl)-benzamide To a stirred solution of 79 mg (0.56 mmol) 4-fluorobenzoic acid in 4 ml THF were added 225 mg (0.59 mmol) HATU and 0.12 ml (1.13 mmol) N-methylmorpholine and stirring continued at 30° C. for 8 h. 75 mg (0.28 mmol) 7-methoxy-4-morpholin-4-yl-thiazolo[5,4-c]pyridin-2-ylamine was then added and stirring continued at 35° C. for 48 h. The reaction mixture was then partitioned between tetrahydrofuran and saturated brine. The organic phases was dried over sodium sulfate and concentrated in vacuo. Flash chromatography (ethyl acetate/heptane) followed by trituration in ether afforded 62 mg (56%) 4-fluoro-N-(7-methoxy-4-morpholin-4-yl-thiazolo[5,4-c]pyridin-2-yl)-benzamide as a white crystalline solid. ES-MS m/e (%): 389 (M+H$^+$, 100).

In an analogous manner there were obtained:

Example 2

N-(7-Methoxy-4-morpholin-4-yl-thiazolo[5,4-c]pyridin-2-yl)-benzamide

From benzoic acid, HATU and N-methylmorpholine in THF, then treatment with 7-methoxy-4-morpholin-4-yl-thiazolo[5,4-c]pyridin-2-ylamine. ES-MS m/e (%): 371 (M+H$^+$, 100).

Example 3

4-Methoxy-N-(7-methoxy-4-morpholin-4-yl-thiazolo[5,4-c]pyridin-2-yl)-benzamide

From 4-methoxybenzoic acid, HATU and N-methylmorpholine in THF, then treatment with 7-methoxy-4-morpholin-4-yl-thiazolo[5,4-c]pyridin-2-ylamine. ES-MS m/e (%): 401 (M+H$^+$, 100).

Example 4

N-(7-Methoxy-4-morpholin-4-yl-thiazolo[5,4-c]pyridin-2-yl)-2-methyl-isonicotinamide From 2-methyl-isonicotinic acid hydrochloride, HATU and N-methylmorpholine in THF, then treatment with 7-methoxy-4-morpholin-4-yl-thiazolo[5,4-c]pyridin-2-ylamine. ES-MS m/e (%): 386 (M+H$^+$, 100).

Example 5

2-Methoxy-N-(7-methoxy-4-morpholin-4-yl-thiazolo[5,4-c]pyridin-2-yl)-isonicotinamide From 2-methoxy-isonicotinic acid hydrochloride, HATU and N-methylmorpholine in THF, then treatment with 7-methoxy-4-morpholin-4-yl-thiazolo[5,4-c]pyridin-2-ylamine. ES-MS m/e (%): 402 (M+H$^+$, 100).

Example 6

3-Fluoro-N-(7-methoxy-4-morpholin-4-yl-thiazolo[5,4-c]pyridin-2-yl)-benzamide

From 3-fluorobenzoic acid, HATU and N-methylmorpholine in THF, then treatment with 7-methoxy-4-morpholin-4-yl-thiazolo[5,4-c]pyridin-2-ylamine. ES-MS m/e (%): 389 (M+H$^+$, 100).

Example 7

3-Methoxy-N-(7-methoxy-4-morpholin-4-yl-thiazolo[5,4-c]pyridin-2-yl)-benzamide

From 3-methoxybenzoic acid, HATU and N-methylmorpholine in THF, then treatment with 7-methoxy-4-morpholin-4-yl-thiazolo[5,4-c]pyridin-2-ylamine. ES-MS m/e (%): 401 (M+H$^+$, 100).

Example 8

3,4-Dimethoxy-N-(7-methoxy-4-morpholin-4-yl-thiazolo[5,4-c]pyridin-2-yl)-benzamide From 3,4-dimethoxybenzoic acid, HATU and N-methylmorpholine in THF, then treatment with 7-methoxy-4-morpholin-4-yl-thiazolo[5,4-c]pyridin-2-ylamine. ES-MS m/e (%): 431 (M+H$^+$, 100).

Example 9

Benzo[1,3]dioxole-5-carboxylic acid (7-methoxy-4-morpholin-4-yl-thiazolo[5,4-c]pyridin-2-yl)-amide From piperonylic acid, HATU and N-methylmorpholine in THF, then treatment with 7-methoxy-4-morpholin-4-yl-thiazolo[5,4-c]pyridin-2-ylamine. ES-MS m/e (%): 415 (M+H$^+$, 100).

Example 10

3-Methoxy-N-(7-methoxy-4-morpholin-4-yl-thiazolo[5,4-c]pyridin-2-yl)-4-methylbenzamide From 3-methoxy-4-methylbenzoic acid, HATU and N-methylmorpholine in THF, then treatment with 7-methoxy-4-morpholin-4-yl-thiazolo[5,4-c]pyridin-2-ylamine. ES-MS m/e (%): 415 (M+H$^+$, 100).

Example 11

N-(7-Methoxy-4-morpholin-4-yl-thiazolo[5,4-c]pyridin-2-yl)-2-(tetrahydro-pyran-4-yl)-acetamide From tetrahydropyran-4-yl-acetic acid, HATU and N-methylmorpholine in THF, then treatment with 7-methoxy-4-morpholin-4-yl-thiazolo[5,4-c]pyridin-2-ylamine. ES-MS m/e (%): 393 (M+H$^+$, 100).

Example 12

N-(7-Methoxy-4-morpholin-4-yl-thiazolo[5,4-c]pyridin-2-yl)-2-phenyl-acetamide

From phenylacetic acid, HATU and N-methylmorpholine in THF, then treatment with 7-methoxy-4-morpholin-4-yl-thiazolo[5,4-c]pyridin-2-ylamine. ES-MS m/e (%): 385 (M+H$^+$, 100).

Example 13

2-Methoxy-N-(7-methoxy-4-morpholin-4-yl-thiazolo[5,4-c]pyridin-2-yl)-acetamide

From methoxyacetic acid, HATU and N-methylmorpholine in THF, then treatment with 7-methoxy-4-morpholin-4-yl-thiazolo[5,4-c]pyridin-2-ylamine. ES-MS m/e (%): 339 (M+H$^+$, 100).

Example 14

3-Methoxy-N-(7-methoxy-4-morpholin-4-yl-thiazolo[5,4-c]pyridin-2-yl)-propionamide From 3-methoxypropionic acid, HATU and N-methylmorpholine in THF, then treatment with 7-methoxy-4-morpholin-4-yl-thiazolo[5,4-c]pyridin-2-ylamine. ES-MS m/e (%): 353 (M+H$^+$, 100).

Example 15

2-Cyclohexyl-N-(7-methoxy-4-morpholin-4-yl-thiazolo[5,4-c]pyridin-2-yl)-acetamide From cyclohexylacetic acid, HATU and N-methylmorpholine in THF, then treatment with 7-methoxy-4-morpholin-4-yl-thiazolo[5,4-c]pyridin-2-ylamine. ES-MS m/e (%): 391 (M+H$^+$, 100).

Example 16

Cyclohexanecarboxylic Acid (7-methoxy-4-morpholin-4-yl-thiazolo[5,4-c]pyridin-2-yl)amide From cyclohexanecarboxylic acid, HATU and N-methylmorpholine in THF, then treatment with 7-methoxy-4-morpholin-4-yl-thiazolo[5,4-c]pyridin-2-ylamine. ES-MS m/e (%): 377 (M+H$^+$, 100).

Example 17

N-(7-Methoxy-4-morpholin-4-yl-thiazolo[5,4-c]pyridin-2-yl)-isonicotinamide

From isonicotinic acid, HATU and N-methylmorpholine in THF, then treatment with 7-methoxy-4-morpholin-4-yl-thiazolo[5,4-c]pyridin-2-ylamine. ES-MS m/e (%): 372 (M+H$^+$, 100).

Example 18

2-(3-Hydroxy-azetidin-1-yl)-N-(7-methoxy-4-morpholin-4-yl-thiazolo[5,4-c]pyridin-2-yl)-isonicotinamide a) 2-Bromo-N-(7-methoxy-4-morpholin-4-yl-thiazolo[5,4-c]pyridin-2-yl)-isonicotinamide To a stirred solution of 455 mg (2.25 mmol) 2-bromo-isonicotinic acid in 8 ml THF were added 914 mg (2.40 mmol) HATU and 0.50 ml (4.51 mmol) N-methylmorpholine and stirring continued at 50° C. for 16 h. 200 mg (0.75 mmol) 7-methoxy-4-morpholin-4-yl-thiazolo[5,4-c]pyridin-2-ylamine was then added and stirring continued at 60° C. for 4 h. The reaction mixture was then concentrated in vacuo. Flash chromatography (methanol/dichloromethane) afforded 208 mg (62%) 2-bromo-N-(7-methoxy-4-morpholin-4-yl-thiazolo[5,4-c]pyridin-2-yl)-isonicotinamide as a yellow crystalline solid. ES-MS m/e (%): 452 (M{$^{81}$Br}+H$^+$, 95), 450 (M{$^{79}$Br}+H$^+$, 100).

b) 2-(3-Hydroxy-azetidin-1-yl)-N-(7-methoxy-4-morpholin-4-yl-thiazolo[5,4-c]pyridin-2-yl)-isonicotinamide A stirred suspension of 200 mg (0.44 mmol) 2-bromo-N-(7-methoxy-4-morpholin-4-yl-thiazolo[5,4-c]pyridin-2-yl)-isonicotinamide, 487 mg (4.44 mmol) azetidin-3-ol hydrochloride and 2.17 g (6.66 mmol) cesium carbonate in 6 ml N-methyl-pyrrolidone in a thick-walled glass pressure tube fitted with a teflon cap was heated at 150° C. for 6 h. The reaction mixture was then cooled to room temperature and partitioned between ethyl acetate and brine. The organic phase was dried over sodium sulfate and concentrated in vacuo. Flash chromatography (methanol/dichloromethane) followed by trituration in ether afforded 29 mg (15%) 2-(3-hydroxy-azetidin-1-yl)-N-(7-methoxy-4-morpholin-4-yl-thiazolo[5,4-c]pyridin-2-yl)-isonicotinamide as a brown crystalline solid. ES-MS m/e (%): 443 (M+H$^+$, 100).

In an analogous manner there was obtained:

Example 19

2-(3-Methoxy-azetidin-1-yl)-N-(7-methoxy-4-morpholin-4-yl-thiazolo[5,4-c]pyridin-2-yl)-isonicotinamide From 2-bromo-N-(7-methoxy-4-morpholin-4-yl-thiazolo[5,4-c]pyridin-2-yl)isonicotinamide with cesium carbonate and 3-methoxy-azetidine hydrochloride. ES-MS m/e (%): 457 (M+H$^+$, 100).

Analogously to Example 1 there were obtained

Example 20

4-(2-Methoxy-ethoxy)-N-(7-methoxy-4-morpholin-4-yl-thiazolo[5,4-c]pyridin-2-yl)-benzamide From 4-(2-methoxy-ethoxy)-benzoic acid, HATU and N-methylmorpholine in THF, then treatment with 7-methoxy-4-morpholin-4-yl-thiazolo[5,4-c]pyridin-2-ylamine. ES-MS m/e (%): 445 (M+H$^+$, 100).

Example 21

6-Methoxy-N-(7-methoxy-4-morpholin-4-yl-thiazolo[5,4-c]pyridin-2-yl)-nicotinamide From 6-methoxynicotinic acid, HATU and N-methylmorpholine in THF, then treatment with 7-methoxy-4-morpholin-4-yl-thiazolo[5,4-c]pyridin-2-ylamine. ES-MS m/e (%): 402 (M+H$^+$, 100).

Analogously to Example 18 there was obtained

Example 22

N-(7-Methoxy-4-morpholin-4-yl-thiazolo[5,4-c]pyridin-2-yl)-2-morpholin-4-yl-isonicotinamide From 2-bromo-N-(7-methoxy-4-morpholin-4-yl-thiazolo[5,4-c]pyridin-2-yl)-isonicotinamide with cesium carbonate in morpholine. ES-MS m/e (%): 457 (M+H$^+$, 100).

Example 23

Morpholine-4-carboxylic acid (7-methoxy-4-morpholin-4-yl-thiazolo[5,4-c]pyridin-2-yl)-amide a) (7-Methoxy-4-morpholin-4-yl-thiazolo[5,4-c]pyridin-2-yl)-carbamic Acid Phenyl Ester To a stirred suspension of 500 mg (1.88 mmol) 7-methoxy-4-morpholin-4-yl-thiazolo[5,4-c]pyridin-2-ylamine and 0.46 ml (5.63 mmol) pyridine in 15 ml dichloromethane and 5 ml tetrahydrofuran was added 0.28 ml (2.25 mmol) phenyl chloroformate and stirring continued at 50° C. for 3 h. The reaction mixture was then filtered and the filtrate concentrated in vacuo. Flash chromatography (ethyl acetate/heptane) afforded 535 mg 74%) (7-methoxy-4-morpholin-4-yl-thiazolo[5,4-c]pyridin-2-yl)-carbamic acid phenyl ester as a white solid. ES-MS m/e (%): 387 (M+H$^+$, 100).

b) Morpholine-4-carboxylic Acid (7-methoxy-4-morpholin-4-yl-thiazolo[5,4-c]pyridin-2-yl)-amide To a stirred solution of 145 mg (0.38 mmol) (7-methoxy-4-morpholin-4-yl-thiazolo[5,4-c]pyridin-2-yl)-carbamic acid phenyl ester in 6 ml dichloroethane and 2 ml tetrahydrofuran at room temperature was added 0.16 ml (1.88 mmol) morpholine and stirring continued at 50° C. for 16 h. The reaction mixture was then concentrated in vacuo. Flash chromatography (ethyl acetate/heptane) followed by trituration in ether afforded 48 mg (34%) morpholine-4-carboxylic acid (7-methoxy-4-morpholin-4-yl-thiazolo[5,4-c]pyridin-2-yl)-amide as a white crystalline solid. ES-MS m/e (%): 380 (M+H$^+$, 100).

In an analogous manner there were obtained:

Example 24

4-Hydroxy-piperidine-1-carboxylic Acid (7-methoxy-4-morpholin-4-yl-thiazolo[5,4-c]pyridin-2-yl)-amide From (7-methoxy-4-morpholin-4-yl-thiazolo[5,4-c]pyridin-2-yl)-carbamic acid phenyl ester with 4-hydroxypiperidine in dichloroethane and tetrahydrofuran. ES-MS m/e (%): 394 (M+H$^+$, 100).

Example 25

4-Hydroxy-4-methyl-piperidine-1-carboxylic acid (7-methoxy-4-morpholin-4-yl-thiazolo[5,4-c]pyridin-2-yl)-amide From (7-methoxy-4-morpholin-4-yl-thiazolo[5,4-c]pyridin-2-yl)-carbamic acid phenyl ester with 4-methyl-piperidin-4-ol in dichloroethane and tetrahydrofuran. ES-MS m/e (%): 408 (M+H$^+$, 100).

Example 26

Cis-1-(4-Hydroxy-cyclohexyl)-3-(7-methoxy-4-morpholin-4-yl-thiazolo[5,4-c]pyridin-2-yl)-1-methyl-urea From (7-methoxy-4-morpholin-4-yl-thiazolo[5,4-c]pyridin-2-yl)-carbamic acid phenyl ester with cis-4-Methylamino-cyclohexanol in dichloroethane and tetrahydrofuran. ES-MS m/e (%): 422 (M+H$^+$, 100).

Example 27

Trans-1-(4-Hydroxy-cyclohexyl)-3-(7-methoxy-4-morpholin-4-yl-thiazolo[5,4-c]pyridin-2-yl)-1-methyl-urea From (7-methoxy-4-morpholin-4-yl-thiazolo[5,4-c]pyridin-2-yl)-carbamic acid phenyl ester with trans-4-Methylamino-cyclohexanol in dichloroethane and tetrahydrofuran. ES-MS m/e (%): 422 (M+H$^+$, 100).

Analogously to Example 1 there were obtained

Example 28

Tetrahydro-pyran-4-carboxylic acid (7-methoxy-4-morpholin-4-yl-thiazolo[5,4-c]pyridin-2-yl)-amide From tetrahydro-pyran-4-yl-carboxylic acid, HATU and N-methylmorpholine in THF, then treatment with 7-methoxy-4-morpholin-4-yl-thiazolo[5,4-c]pyridin-2-ylamine. ES-MS m/e (%): 379 (M+H$^+$, 100).

Example 29

N-(7-Methoxy-4-morpholin-4-yl-thiazolo[5,4-c]pyridin-2-yl)-4-morpholin-4-yl-benzamide From 4-morpholin-4-yl-benzoic acid, HATU and N-methylmorpholine in THF, then treatment with 7-methoxy-4-morpholin-4-yl-thiazolo[5,4-c]pyridin-2-ylamine. ES-MS m/e (%): 456 (M+H$^+$, 100).

Example 30

N-(7-Methoxy-4-morpholin-4-yl-thiazolo[5,4-c]pyridin-2-yl)-3-morpholin-4-yl-benzamide From 3-morpholin-4-yl-benzoic acid, HATU and N-methylmorpholine in THF, then treatment with 7-methoxy-4-morpholin-4-yl-thiazolo[5,4-c]pyridin-2-ylamine. ES-MS m/e (%): 456 (M+H$^+$, 100).

Example 31

4-{[(2-Methoxy-ethyl)-methyl-amino]-methyl}-N-(7-methoxy-4-morpholin-4-yl-thiazolo[5,4-c]pyridin-2-yl)-benzamide a) 4-Chloromethyl-N-(7-methoxy-4-morpholin-4-yl-thiazolo[5,4-c]pyridin-2-yl)-benzamide To a stirred suspension of 150 mg (0.56 mmol) 7-methoxy-4-morpholin-4-yl-thiazolo[5,4-c]pyridin-2-ylamine in 3 ml 1,2-dichloroethane and 3 ml THF at room temperature were added 0.29 ml (1.69 mmol) N-ethyldiisopropylamine and 117 mg (0.62 mmol) 4-(chloromethyl)benzoyl chloride and stirring continued at 80° C. for 2 h. The reaction mixture was then cooled to room temperature and concentrated in vacuo. Flash chromatography (ethyl acetate/heptane) afforded 157 mg (67%) 4-chloromethyl-N-(7-methoxy-4-morpholin-4-yl-thiazolo[5,4-c]pyridin-2-yl)-benzamide as a yellow solid. ES-MS m/e (%):421 (M{$^{37}$Cl}+H$^+$, 35), 419 (M{$^{35}$Cl}+H$^+$, 100).

b) 4-{[(2-Methoxy-ethyl)-methyl-amino]-methyl}-N-(7-methoxy-4-morpholin-4-yl-thiazolo[5,4-c]pyridin-2-yl)-benzamide A solution of 60 mg (0.14 mmol) 4-chloromethyl-N-(7-methoxy-4-morpholin-4-yl-thiazolo[5,4-c]pyridin-2-yl)-benzamide in 0.30 ml (2.70 mmol) N-(2-methoxyethyl)methylamine was ultrasonicated at room temperature for 40 min. The reaction mixture was then concentrated in vacuo. Flash chromatography (methanol/dichloromethane) followed by trituration in ether afforded 41 mg (61%) 4-{[(2-methoxy-ethyl)-methyl-amino]-methyl}-N-(7-methoxy-4-morpholin-4-yl-thiazolo[5,4-c]pyridin-2-yl)-benzamide as a white crystalline solid. ES-MS m/e (%): 472 (M+H$^+$, 100).

In an analogous manner there were obtained:

Example 32

N-(7-Methoxy-4-morpholin-4-yl-thiazolo[5,4-c]pyridin-2-yl)-2-morpholin-4-yl-acetamide From 7-methoxy-4-morpholin-4-yl-thiazolo[5,4-c]pyridin-2-ylamine with chloroacetyl chloride and N-ethyldiisopropylamine in 1,2-dichloroethane and THF; then subsequent treatment with morpholine. ES-MS m/e (%): 394 (M+H$^+$, 100).

Example 33

N-(7-Methoxy-4-morpholin-4-yl-thiazolo[5,4-c]pyridin-2-yl)-2-morpholin-4-ylmethyl-isonicotinamide From 7-methoxy-4-morpholin-4-yl-thiazolo[5,4-c]pyridin-2-ylamine with 2-chloromethyl-isonicotinoyl chloride and N-ethyldiisopropylamine in 1,2-dichloroethane and THF; then subsequent treatment with morpholine. ES-MS m/e (%): 471 (M+H$^+$, 100).

Example 34

2-Diethylaminomethyl-N-(7-methoxy-4-morpholin-4-yl-thiazolo[5,4-c]pyridin-2-yl)isonicotinamide From 7-methoxy-4-morpholin-4-yl-thiazolo[5,4-c]pyridin-2-ylamine with 2-chloromethyl-isonicotinoyl chloride and N-ethyldiisopropylamine in 1,2-dichloroethane and THF; then subsequent treatment with diethylamine in NMP. ES-MS m/e (%): 457 (M+H$^+$, 100).

Example 35

2-(4-Hydroxy-piperidin-1-ylmethyl)-N-(7-methoxy-4-morpholin-4-yl-thiazolo[5,4-c]pyridin-2-yl)-isonicotinamide From 7-methoxy-4-morpholin-4-yl-thiazolo[5,4-c]pyridin-2-ylamine with 2-chloromethyl-isonicotinoyl chloride and N-ethyldiisopropylamine in 1,2-dichloroethane and THF; then subsequent treatment with 4-hydroxypiperidine in NMP. ES-MS m/e (%): 485 (M+H$^+$, 100).

Analogously to Example 23 there were obtained

Example 36

4-Hydroxymethyl-piperidine-1-carboxylic acid (7-methoxy-4-morpholin-4-yl-thiazolo[5,4-c]pyridin-2-yl)-amide From (7-methoxy-4-morpholin-4-yl-thiazolo[5,4-c]pyridin-2-yl)-carbamic acid phenyl ester with 4-(hydroxymethyl)piperidine and pyridine in dichloroethane and tetrahydrofuran. ES-MS m/e (%): 408 (M+H$^+$, 100).

Example 37

2-Methyl-1-oxo-2,8-diaza-spiro [4.5] decane-8-carboxylic acid (7-methoxy-4-morpholin-4-yl-thiazolo[5,4-c]pyridin-2-yl)-amide From (7-methoxy-4-morpholin-4-yl-thiazolo[5,4-c]pyridin-2-yl)-carbamic acid phenyl ester with 4-spiro-[3-(N-methyl-2-pyrrolidone)]-piperidine hydrochloride and pyridine in dichloroethane and tetrahydrofuran. ES-MS m/e (%): 461 (M+H$^+$, 100).

Example 38

(1S,4S)-2-Oxa-5-aza-bicyclo [2.2.1]heptane-5-carboxylic acid (7-methoxy-4-morpholin-4-yl-thiazolo[5,4-c]pyridin-2-yl)-amide From (7-methoxy-4-morpholin-4-yl-thiazolo[5,4-c]pyridin-2-yl)-carbamic acid phenyl ester with (1S,4S)-2-oxa-5-aza-bicyclo[2.2.1]heptane trifluoroacetate and N,N-diisopropylethylamine in dichloroethane and tetrahydrofuran. ES-MS m/e (%): 392 (M+H$^+$, 100).

Analogously to Example 31 there was obtained

Example 39

N-(7-Methoxy-4-morpholin-4-yl-thiazolo[5,4-c]pyridin-2-yl)-4-morpholin-4-ylmethyl-benzamide From 7-methoxy-4-morpholin-4-yl-thiazolo[5,4-c]pyridin-2-ylamine with 4-(chloromethyl)benzoyl chloride and N-ethyldiisopropylamine in 1,2-dichloroethane and THF; then subsequent treatment with morpholine. ES-MS m/e (%): 470 (M+H$^+$, 100).

Analogously to Example 23 there were obtained

Example 40

1-Oxa-8-aza-spiro[4.5]decane-8-carboxylic acid (7-methoxy-4-morpholin-4-yl-thiazolo[5,4-c]pyridin-2-yl)-amide From (7-methoxy-4-morpholin-4-yl-thiazolo[5,4-c]pyridin-2-yl)-carbamic acid phenyl ester with 1-oxa-8-aza-spiro[4.5]decane trifluoroacetate and N,N-diisopropylethylamine in dichloroethane and tetrahydrofuran. ES-MS m/e (%): 434 (M+H$^+$, 100).

Example 41 cis-1-(4-Hydroxy-4-methyl-cyclohexyl)-3-(7-methoxy-4-morpholin-4-yl-thiazolo[5,4-c]pyridin-2-yl)-1-methyl-urea From (7-methoxy-4-morpholin-4-yl-thiazolo[5,4-c]pyridin-2-yl)-carbamic acid phenyl ester with 1-methyl-4-cis-methylamino-cyclohexanol and N,N-diisopropylethylamine in dichloroethane and tetrahydrofuran. ES-MS m/e (%): 436 (M+H$^+$, 100).

Example 42

4-Methoxymethyl-piperidine-1-carboxylic acid (7-methoxy-4-morpholin-4-yl-thiazolo[5,4-c]pyridin-2-yl)-amide From (7-methoxy-4-morpholin-4-yl-thiazolo[5,4-c]pyridin-2-yl)-carbamic acid phenyl ester with 4-methoxymethyl-piperidine trifluoroacetate and N,N-diisopropylethylamine in dichloroethane and tetrahydrofuran. ES-MS m/e (%): 422 (M+H$^+$, 100).

Example 43

4-Hydroxymethyl-4-methyl-piperidine-1-carboxylic acid (7-methoxy-4-morpholin-4-yl-thiazolo[5,4-c]pyridin-2-yl)-amide From (7-methoxy-4-morpholin-4-yl-thiazolo[5,4-c]pyridin-2-yl)-carbamic acid phenyl ester with (4-methyl-piperidin-4-yl)-methanol trifluoroacetate and N,N-diisopropylethylamine in dichloroethane and tetrahydrofuran. ES-MS m/e (%): 422 (M+H$^+$, 100).

Example 44

4-Methoxymethyl-4-methyl-piperidine-1-carboxylic acid (7-methoxy-4-morpholin-4-yl-thiazolo[5,4-c]pyridin-2-yl)-amide From (7-methoxy-4-morpholin-4-yl-thiazolo[5,4-c]pyridin-2-yl)-carbamic acid phenyl ester with 4-methoxymethyl-4-methyl-piperidine trifluoroacetate and N,N-diisopropylethylamine in dichloroethane and tetrahydrofuran. ES-MS m/e (%): 436 (M+H$^+$, 100).

Example 45

N-(7-Methoxy-4-phenyl-thiazolo[5,4-c]pyridin-2-yl)-benzamide a) 2-Phenyl-pyridin-4-ylamine To a stirred solution of 16.0 g (124 mmol) 2-chloro-4-aminopyridine in 200 ml toluene were added 18.2 g (149 mmol) phenylboronic acid, 7.19 g (6.22 mmol) tetrakis (triphenylphosphine)palladium(0) and 130 ml (260 mmol) 2 M aq. sodium carbonate solution. The mixture was heated at 100° C. for 16 h and then cooled to room temperature and extracted three times with ethyl acetate. The combined organic phases were extracted three times with 200 ml 1 M aq. hydrochloric acid. The combined acid extracts were then made alkaline by addition of 5 M aq. sodium hydroxide solution and extracted three times with dichloromethane. The combined organic extracts were dried over sodium sulfate, and concentrated in vacuo. Flash chromatography (acetone) followed by trituration in hexane containing a little ether afforded 18.5 g (87%) 2-phenyl-pyridin-4-ylamine as a white solid. ES-MS m/e (%): 171 (M+H$^+$, 100).

b) 5-Iodo-2-phenyl-pyridin-4-ylamine

To a stirred solution of 10.0 g (58.8 mmol) 2-phenyl-pyridin-4-ylamine in 300 ml glacial acetic acid was added 28.9 g (352 mmol) sodium acetate and the mixture was then cooled to 15° C. in an ice-bath and 19.1 g (118 mmol) iodine monochloride added in small portions (reaction slightly exothermic). The reaction mixture was stirred for 48 h at room temperature before being poured onto 500 ml 20% aq. sodium thiosulfate solution. The mixture was then made basic by addition of 5 N aq. sodium hydroxide solution and extracted three times with dichloromethane. The combined organic phases were washed with 20% aq. sodium thiosulfate solution, then dried over sodium sulfate and concentrated in vacuo. Flash chromatography (methanol/dichloromethane 3/97) followed by trituration in ether afforded 9.90 g (57%) 5-iodo-2-phenyl-pyridin-4-ylamine as an off-white solid. ES-MS m/e (%): 297 (M+H$^+$, 100).

c) 5-Methoxy-2-phenyl-pyridin-4-ylamine

A stirred suspension of 6.20 g (20.9 mmol) 5-iodo-2-phenyl-pyridin-4-ylamine, 319 mg (1.68 mmol) copper(I) iodide, 453 mg (2.51 mmol) 1,10-phenanthroline and 13.6 g (41.9 mmol) cesium carbonate in 40 ml methanol was heated at 130° C. for 20 min in a microwave oven. The resulting mixture was then cooled to room temperature and concentrated in vacuo. The residue was resuspended in 500 ml dichloromethane and extracted three times with 200 ml portions of 1 M aq. hydrochloric acid. The combined acid extracts were then made basic by addition of 5 N aq. sodium hydroxide solution and extracted three times with dichloromethane. The combined organic phases were dried over sodium sulfate and concentrated in vacuo. Flash chromatography (methanol/dichloromethane 3/97-5/95) afforded 1.87 g (45%) 5-methoxy-2-phenyl-pyridin-4-ylamine as a dark red oil. ES-MS m/e (%): 201 (M+H$^+$, 100).

d) 3-Iodo-5-methoxy-2-phenyl-pyridin-4-ylamine

To an ice-cooled stirred suspension of 2.70 g (6.20 mmol) 5-methoxy-2-phenyl-pyridin-4-ylamine in 3 ml distilled water was added dropwise 3 ml concentrated sulfuric acid and the mixture was then warmed to 100° C. 1.30 g (6.07 mmol) potassium iodate was added after 3 h, a further 1.30 g (6.07 mmol) potassium iodate was added after an additional 3 h, and finally a further 0.75 g (3.50 mmol) potassium iodate was added after an additional 3 h. Stirred was continued for a further 2.5 h at 100° C., and then the mixture was allowed to cool to room temperature on standing overnight. The mixture was then diluted with saturated brine, made basic by addition of 30% aq. sodium hydroxide solution, and extracted three times with tetrahydrofuran. The combined organic phases were dried over sodium sulfate and concentrated in vacuo. Flash chromatography (ethyl acetate/heptane) afforded 1.60 g (79%) 3-iodo-5-methoxy-2-phenyl-pyridin-4-ylamine as an orange oil which crystallized on standing. ES-MS m/e (%): 327 (M+H$^+$, 100).

e) 1-Benzoyl-3-(3-iodo-5-methoxy-2-phenyl-pyridin-4-yl)-thiourea

To a stirred solution of 159 g (4.88 mmol) 3-iodo-5-methoxy-2-phenyl-pyridin-4-ylamine in 30 ml acetone was added dropwise 0.98 ml (7.31 mmol) benzoyl isothiocyanate at room temperature. The reaction mixture then heated at reflux for 5 h before being cooled to room temperature concentrated in vacuo. Flash chromatography (ethyl acetate/heptane) afforded 1.61 g (67%) 1-benzoyl-3-(3-iodo-5-methoxy-2-phenyl-pyridin-4-yl)-thiourea as a yellow crystalline solid. ES-MS m/e (%): 490 (M+H$^+$, 100).

f) N-(7-Methoxy-4-phenyl-thiazolo[5,4-c]pyridin-2-yl)-benzamide

A stirred suspension of 600 mg (1.23 mmol) 1-benzoyl-3-(3-iodo-5-methoxy-2-phenyl-pyridin-4-yl)-thiourea, 23 mg (0.12 mmol)-copper(I) iodide, 44 mg (0.25 mmol) 1,10-phenanthroline and 799 mg (2.45 mmol) cesium carbonate in 4 ml toluene was heated at 130° C. for 2×5 min in a microwave oven. The resulting mixture was then cooled to room temperature and diluted with tetrahydrofuran, stirred and filtered. The filter cake was washed with tetrahydrofuran and the combined filtrate and washings were concentrated in vacuo. Flash chromatography (ethyl acetate/heptane) afforded 361 mg (81%) N-(7-methoxy-4-phenyl-thiazolo[5,4-c]pyridin-2-yl)-benzamide as a white solid. ES-MS m/e (%): 362 (M+H$^+$, 100).

Example 46

4-Fluoro-N-(7-methoxy-4-phenyl-thiazolo[5,4-c]pyridin-2-yl)-benzamide a) 7-Methoxy-4-phenyl-thiazolo[5,4-c]pyridin-2-ylamine To a stirred suspension of 360 mg (1.00 mmol) N-(7-methoxy-4-phenyl-thiazolo[5,4-c]pyridin-2-yl)-benzamide in 3 ml methanol was added 1 ml 5 N aq. sodium hydroxide solution and the resulting solution was then heated at 130° C. for 10 min in a microwave oven. The reaction mixture was then cooled to room temperature and concentrated in vacuo. Flash chromatography (ethyl acetate/heptane) afforded 122 mg (48%) 7-methoxy-4-phenyl-thiazolo[5,4-c]pyridin-2-ylamine as a white crystalline solid. ES-MS m/e (%): 258 (M+H$^+$, 100).

b) 4-Fluoro-N-(7-methoxy-4-phenyl-thiazolo[5,4-c]pyridin-2-yl)-benzamide

To a stirred solution of 44 mg (0.31 mmol) 4-fluoro-benzoic acid in 4 ml THF were added 130 mg (0.34 mmol) HATU and 0.068 ml (0.62 mmol) N-methylmorpholine and stirring continued at 50° C. for 16 h. 40 mg (0.16 mmol) 7-methoxy-4-phenyl-thiazolo[5,4-c]pyridin-2-ylamine was then added and stirring continued at 50° C. for 16 h. The reaction mixture was then concentrated in vacuo. Flash chromatography (ethyl acetate/heptane) followed by trituration in ether afforded 7 mg (12%) 4-fluoro-N-(7-methoxy-4-phenyl-thiazolo[5,4-c]pyridin-2-yl)-benzamide as a white crystalline solid. ES-MS m/e (%): 380 (M+H$^+$, 100).

In an analogous manner there were obtained:

Example 47

N-(7-Methoxy-4-phenyl-thiazolo[5,4-c]pyridin-2-yl)-2-morpholin-4-yl-isonicotinamide From 2-(4-morpholinyl)-4-pyridinecarboxylic acid, HATU and N-methylmorpholine in THF, then treatment with 7-methoxy-4-phenyl-thiazolo[5,4-c]pyridin-2-ylamine. ES-MS m/e (%): 448 (M+H$^+$, 100).

Example 48

N-(7-Methoxy-4-phenyl-thiazolo[5,4-c]pyridin-2-yl)-2-methyl-isonicotinamide

From 2-methyl-isonicotinic acid hydrochloride, HATU and N-methylmorpholine in THF, then treatment with 7-methoxy-4-phenyl-thiazolo[5,4-c]pyridin-2-ylamine. ES-MS m/e (%): 377 (M+H$^+$, 100).

Example 49

3-Methoxy-N-(7-methoxy-4-phenyl-thiazolo[5,4-c]pyridin-2-yl)-benzamide

From 3-methoxybenzoic acid, HATU and N-methylmorpholine in THF, then treatment with 7-methoxy-4-phenyl-thiazolo[5,4-c]pyridin-2-ylamine. ES-MS m/e (%): 392 (M+H$^+$, 100).

Example 50

Cyclohexanecarboxylic Acid (7-methoxy-4-phenyl-thiazolo[5,4-c]pyridin-2-yl)-amide From cyclohexanecarboxylic acid, HATU and N-methylmorpholine in THF, then treatment with 7-methoxy-4-phenyl-thiazolo[5,4-c]pyridin-2-ylamine. ES-MS m/e (%): 371 (M+H$^+$, 100).

Example 51

N-[7-Methoxy-4-(tetrahydro-pyran-4-yl)-thiazolo[5,4-c]pyridin-2-yl]-benzamide a) 2-(3,6-Dihydro-2H-pyran-4-yl)-4-nitro-pyridine To a stirred solution of 7.00 g (44.2 mmol) 2-chloro-4-nitropyridine in 150 ml N,N-dimethylformamide were added 16.8 g (45.0 mmol) tributyl-(3,6-dihydro-2H-pyran-4-yl)stannane, 3.72 g (5.30 mmol) bis(triphenylphosphine) palladium(II) chloride, 6.95 g (26.5 mmol) triphenylphosphine, 15.0 g (353 mmol) lithium chloride and 0.97 g (4.42 mmol) 2,6-di-tert-butyl-p-cresol. The mixture was heated at 100° C. for 4 h and then cooled to room temperature and concentrated in vacuo. Flash chromatography (heptane/ethyl acetate 9/1 then ethyl acetate) afforded 2.10 g (23%) 2-(3,6-dihydro-2H-pyran-4-yl)-4-nitro-pyridine as an orange solid. ES-MS m/e (%): 207 (M+H$^+$, 100).

b) 2-(Tetrahydro-pyran-4-yl)-pyridin-4-ylamine

To a stirred solution of 550 g (26.7 mmol) 2-(3,6-dihydro-2H-pyran-4-yl)-4-nitro-pyridine in 230 ml tetrahydrofuran and 5 ml glacial acetic acid was added 2.84 g of 10% palladium on charcoal and the mixture was then stirred for 16 h under an atmosphere of hydrogen at room temperature and 1.7 bar pressure. The mixture was then filtered, washing with methanol, and the filtrate concentrated in vacuo. Flash chromatography (methanol/dichloromethane/triethylamine 100/5/1) afforded 4.75 g (100%) 2-(tetrahydro-pyran-4-yl)-pyridin-4-ylamine as a light yellow oil. ES-MS m/e (%): 179 (M+H$^+$, 100).

c) 5-Iodo-2-(tetrahydro-pyran-4-yl)-pyridin-4-ylamine

To a stirred solution of 5.80 g (32.5 mmol) 2-(tetrahydro-pyran-4-yl)-pyridin-4-ylamine in 20 ml 65% aqueous sulfuric acid heated to 135° C. was added 7.66 g (35.8 mmol) potassium iodate and stirring continued for 2.5 h at 135° C. The mixture was then cooled in an ice-bath before being made basic by addition of 5 N aqueous sodium hydroxide solution. The mixture was extracted three times with tetrahydrofuran and the combined organic phases were dried over sodium sulfate and concentrated in vacuo. The residue was resuspended in 200 ml tetrahydrofuran and 200 ml ethyl acetate and then concentrated in vacuo to 70 ml. The resulting crystals were collected by filtration to afford 2.68 g (27%) 5-iodo-2-(tetrahydro-pyran-4-yl)-pyridin-4-ylamine as a white crystalline solid. ES-MS m/e (%): 305 (M+H$^+$, 100). The mother liquor was concentrated in vacuo; flash chromatography (methanol/dichloromethane 1/50 to 1/20) afforded a further 0.79 g (8%) 5-iodo-2-(tetrahydro-pyran-4-yl)-pyridin-4-ylamine as a white crystalline solid, as well as 0.98 g (10%) 3-iodo-2-(tetrahydro-pyran-4-yl)-pyridin-4-ylamine as a white crystalline solid. ES-MS m/e (%): 305 (M+H$^+$, 100).

d) 5-Methoxy-2-(tetrahydro-pyran-4-yl)-pyridin-4-ylamine

A stirred suspension of 1.05 g (3.10 mmol) 5-iodo-2-(tetrahydro-pyran-4-yl)-pyridin-4-ylamine, 59 mg (0.31 mmol) copper(I) iodide, 112 mg (0.62 mmol) 1,10-phenanthroline and 2.02 g (6.19 mmol) cesium carbonate in 5 ml methanol was heated at 130° C. for 2×3 min in a microwave oven. The resulting mixture was then cooled to room temperature and concentrated in vacuo. Flash chromatography (methanol/dichloromethane/triethylamine) afforded 394 mg (57%) 5-methoxy-2-(tetrahydro-pyran-4-yl)-pyridin-4-ylamine as a red crystalline solid. ES-MS m/e (%): 209 (M+H$^+$, 100).

e) 3-Iodo-5-methoxy-2-(tetrahydro-pyran-4-yl)-pyridin-4-ylamine

To a stirred solution of 590 mg (2.66 mmol) 5-methoxy-2-(tetrahydro-pyran-4-yl)-pyridin-4-ylamine in 3 ml 65% aqueous sulfuric acid heated to 100° C. was added 728 mg (3.40 mmol) potassium iodate and stirring continued for 2 h at 100° C. The mixture was then cooled in an ice-bath before being made basic by addition of 5 N aqueous sodium hydroxide solution. The mixture was extracted three times with tetrahydrofuran and the combined organic phases were dried over sodium sulfate and concentrated in vacuo. Flash chromatography (ethyl acetate/hexane/triethylamine) afforded 516 mg (58%) 3-iodo-5-methoxy-2-(tetrahydro-pyran-4-yl)-pyridin-4-ylamine as a yellow crystalline solid. ES-MS m/e (%): 335 (M+H$^+$, 100).

f) 1-Benzoyl-3-[3-iodo-5-methoxy-2-(tetrahydro-pyran-4-yl)-pyridin-4-yl]-thiourea To a stirred solution of 725 mg (2.17 mmol) 3-iodo-5-methoxy-2-(tetrahydro-pyran-4-yl)-pyridin-4-ylamine in 14 ml acetone was added dropwise 0.35 ml (2.60 mmol) benzoyl isothiocyanate at room temperature. The reaction mixture then heated at reflux for 2 h before being cooled to room temperature concentrated in vacuo. Flash chromatography (ethyl acetate/heptane) afforded 868 mg (80%) 1-benzoyl-3-[3-iodo-5-methoxy-2-(tetrahydro-pyran-4-yl)-pyridin-4-yl]-thiourea as a white crystalline solid. ES-MS m/e (%): 498 (M+H$^+$, 100).

g) N-[7-Methoxy-4-(tetrahydro-pyran-4-yl)-thiazolo[5,4-c]pyridin-2-yl]-benzamide A stirred suspension of 760 mg (1.53 mmol) 1-benzoyl-3-[3-iodo-5-methoxy-2-(tetrahydro-pyran-4-yl)-pyridin-4-yl]-thiourea, 29 mg (0.15 mmol) copper(I) iodide, 55 mg (0.31 mmol) 1,10-phenanthroline and 1.00 g (3.06 mmol) cesium carbonate in 4 ml toluene was heated at 130° C. for 10 min in a microwave oven. The resulting mixture was then cooled to room temperature and concentrated in vacuo. The residue was resuspended in methanol, the mixture filtered, and the filtrate concentrated in vacuo. Flash chromatography (ethyl acetate/heptane) afforded 314 mg (56%) N-[7-methoxy-4-(tetrahydro-pyran-4-yl)-thiazolo[5,4-c]pyridin-2-yl]-benzamide as a white solid. ES-MS m/e (%): 370 (M+H$^+$, 100).

Example 52

4-Fluoro-N-[7-methoxy-4-(tetrahydro-pyran-4-yl)-thiazolo[5,4-c]pyridin-2-yl]-benzamide a) 7-Methoxy-4-(tetrahydro-pyran-4-yl)-thiazolo[5,4-c]pyridin-2-ylamine To a stirred suspension of 314 mg (0.85 mmol) N-[7-methoxy-4-(tetrahydro-pyran-4-yl)-thiazolo[5,4-c]pyridin-2-yl]-benzamide in 2.5 ml methanol was added 0.85 ml 5 N aq. sodium hydroxide solution and the resulting solution was then heated at 130° C. for 12 min in a microwave oven. The reaction mixture was then cooled to room temperature and partitioned between tetrahydrofuran and 1 N aq. sodium hydroxide solution. The phases were separated and the organic phase was dried over sodium sulfate and concentrated in vacuo. Flash chromatography (methanol/dichloromethane) afforded 174 mg (77%) 7-methoxy-4-(tetrahydro-pyran-4-yl)-thiazolo[5,4-c]pyridin-2-ylamine as a light yellow crystalline solid. ES-MS m/e (%): 266 (M+H$^+$, 100).

b) 4-Fluoro-N-[7-methoxy-4-(tetrahydro-pyran-4-yl)-thiazolo[5,4-c]pyridin-2-yl]-benzamide To a stirred solution of 42 mg (0.30 mmol) 4-fluorobenzoic acid in 4 ml THF were added 126 mg (0.33 mmol) HATU and 0.066 ml (0.60 mmol) N-methylmorpholine and stirring continued at 50° C. for 6 h. 40 mg (0.15 mmol) 7-methoxy-4-(tetrahydro-pyran-4-yl)-thiazolo[5,4-c]pyridin-2-ylamine was then added and stirring continued at 50° C. for 16 h. The reaction mixture was then concentrated in vacuo. Flash chromatography (ethyl acetate/heptane) followed by trituration in ether afforded 44 mg (75%) 4-fluoro-N-[7-methoxy-4-(tetrahydro-pyran-4-yl)-thiazolo[5,4-c]pyridin-2-yl]-benzamide as a white crystalline solid. ES-MS m/e (%): 388 (M+H$^+$, 100).

In an analogous manner there were obtained:

Example 53

N-[7-Methoxy-4-(tetrahydro-pyran-4-yl)-thiazolo[5,4-c]pyridin-2-yl]-2-morpholin-4-yl-isonicotinamide From 2-(4-morpholinyl)-4-pyridinecarboxylic acid, HATU and N-methylmorpholine in THF, then treatment with 7-methoxy-4-(tetrahydro-pyran-4-yl)thiazolo[5,4-c]pyridin-2-ylamine. ES-MS m/e (%): 456 (M+H$^+$, 100).

Example 54

N-[7-Methoxy-4-(tetrahydro-pyran-4-yl)-thiazolo[5,4-c]pyridin-2-yl]-2-methyl-isonicotinamide From 2-methyl-isonicotinic acid hydrochloride, HATU and N-methylmorpholine in THF, then treatment with 7-methoxy-4-(tetrahydro-pyran-4-yl)-thiazolo[5,4-c]pyridin-2-ylamine. ES-MS m/e (%): 385 (M+H$^+$, 100).

Example 55

3-Methoxy-N-[7-methoxy-4-(tetrahydro-pyran-4-yl)-thiazolo[5,4-c]pyridin-2-yl]-benzamide From 3-methoxybenzoic acid, HATU and N-methylmorpholine in THF, then treatment with 7-methoxy-4-(tetrahydro-pyran-4-yl)-thiazolo[5,4-c]pyridin-2-ylamine. ES-MS m/e (%): 400 (M+H$^+$, 100).

Example 56

Cyclohexanecarboxylic Acid [7-methoxy-4-(tetrahydro-pyran-4-yl)-thiazolo[5,4-c]pyridin-2-yl]-amide From cyclohexanecarboxylic acid, HATU and N-methylmorpholine in THF, then treatment with 7-methoxy-4-(tetrahydro-pyran-4-yl)-thiazolo[5,4-c]pyridin-2-ylamine. ES-MS m/e (%): 376 (M+H$^+$, 100).

Example 57

4-Hydroxymethyl-piperidine-1-carboxylic acid [7-methoxy-4-(tetrahydro-pyran-4-yl)-thiazolo[5,4-c]pyridin-2-yl]-amide To a stirred suspension of 17 mg (0.06 mmol) 7-methoxy-4-(tetrahydro-pyran-4-yl)-thiazolo[5,4-c]pyridin-2-ylamine and 0.015 ml (0.19 mmol) pyridine in 1.5 ml dichloromethane and 0.5 ml tetrahydrofuran was added 0.009 ml (0.07 mmol) phenyl chloroformate and stirring continued at 50° C. for 1 h. 37 mg (0.32 mmol) 4-(hydroxymethyl)piperidine was then added and stirring continued at 50° C. for a further 1 h. The reaction mixture was then concentrated in vacuo. Flash chromatography (methanol/dichloromethane 1/40 then 1/20) afforded 11 mg (42%) 4-hydroxymethylpiperidine-1-carboxylic acid [7-methoxy-4-(tetrahydro-pyran-4-yl)-thiazolo[5,4-c]pyridin-2-yl]-amide as a white crystalline solid. ES-MS m/e (%): 407 (M+H$^+$, 100).

The invention claimed is:
1. A compound of formula I

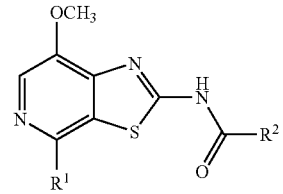

(I)

wherein,
R$^1$ is selected from morpholin-4-yl, phenyl and tetrahydropyran-4-yl;
R$^2$ is selected from
—(CH$_2$)$_n$-aryl;
—(CH$_2$)$_n$-aryl substituted by one or more substituents selected from the group consisting of halogen, lower alkoxy, lower alkyl, —(CH$_2$)$_n$ NR'R", —O(CH$_2$)$_n$—O-lower alkyl, and —(CH$_2$)$_n$-heterocyclyl;

heteroaryl;

heteroaryl substituted by one or more substituents, selected from the group consisting of lower alkyl, lower alkoxy, —(CH$_2$)$_n$NR'R", —(CH$_2$)$_n$-heterocyclyl, and —(CH$_2$)$_n$-heterocyclyl substituted by one or more substituents selected from hydroxy, lower alkoxy, —(CH$_2$)$_n$—OH, —(CH$_2$)$_n$—O-lower alkyl and lower alkyl;

—(CH$_2$)$_n$-cycloalkyl;

—(CH$_2$)$_n$—O-lower alkyl;

NR'R";

benzo[1,3]dioxole;

2-methyl-1-oxo-2,8-diaza-spiro[4,5]decane;

2-oxa-5-aza-bicyclo [2.2.1]heptane; or 1-oxa-8-aza-spiro[4.5]decane;

R' and R" are independently from each other selected from lower alkyl, —(CH$_2$)$_n$-O-lower alkyl, cycloalkyl, and cycloalkyl substituted by hydroxy; and n is 0, 1 or 2;

or a pharmaceutically acceptable salt thereof.

2. The compound of formula I in accordance with claim 1, wherein R$^1$ is morpholinyl and R$^2$ is selected from phenyl, and phenyl substituted by a group selected from halogen, lower alkoxy and morpholinyl.

3. The compound of formula I in accordance with claim 2, wherein the compound is selected from 4-fluoro-N-(7-methoxy-4-morpholin-4-yl-thiazolo[5,4-c]pyridin-2-yl)-benzamide, N-(7-methoxy-4-morpholin-4-yl-thiazolo[5,4-c]pyridin-2-yl)-benzamide, 4-methoxy-N-(7-methoxy-4-morpholin-4-yl-thiazolo[5,4-c]pyridin-2-yl)-benzamide, 3-fluoro-N-(7-methoxy-4-morpholin-4-yl-thiazolo[5,4-c]pyridin-2-yl)-benzamide, 3-methoxy-N-(7-methoxy-4-morpholin-4-yl-thiazolo[5,4-c]pyridin-2-yl)-benzamide, 3-methoxy-N-(7-methoxy-4-morpholin-4-yl-thiazolo[5,4-c]pyridin-2-yl)-4-methylbenzamide, and N-(7-methoxy-4-morpholin-4-yl-thiazolo[5,4-c]pyridin-2-yl)-3-morpholin-4-yl-benzamide.

4. The compound of formula I in accordance with claim 1, wherein R$^1$ is phenyl and R$^2$ is selected from phenyl, phenyl substituted by halogen and phenyl substituted by lower alkoxy.

5. The compound of formula I in accordance with claim 4, wherein the compound is selected from N-(7-methoxy-4-phenyl-thiazolo[5,4-c]pyridin-2-yl)-benzamide, 4-fluoro-N-(7-methoxy-4-phenyl-thiazolo[5,4-c]pyridin-2-yl)-benzamide, and 3-methoxy-N-(7-methoxy-4-phenyl-thiazolo[5,4-c]pyridin-2-yl)-benzamide.

6. The compound of formula I in accordance with claim 1, wherein R$^1$ is morpholinyl, R$^2$ is —(CH$_2$)$_n$-cycloalkyl, and n is 0 or 1.

7. The compound of formula I in accordance with claim 6, wherein the compound is selected from 2-cyclohexyl-N-(7-methoxy-4-morpholin-4-yl-thiazolo[5,4-c]pyridin-2-yl)-acetamide, and cyclohexanecarboxylic acid (7-methoxy-4-morpholin-4-yl-thiazolo[5,4-c]pyridin-2-yl)amide.

8. The compound of formula I in accordance with claim 1, wherein R$^1$ is morpholinyl and R$^2$ is selected from pyridyl, and pyridyl substituted by one or more substituents selected from the group consisting of —(CH$_2$)$_n$-heterocyclyl, —(CH$_2$)$_n$-heterocyclyl substituted by hydroxy, and —(CH$_2$)$_n$-heterocyclyl substituted by lower alkoxy.

9. The compound of formula I in accordance with claim 8, wherein the compound is selected from 2-(3-hydroxy-azetidin-1-yl)-N-(7-methoxy-4-morpholin-4-yl-thiazolo[5,4-c]pyridin-2-yl)-isonicotinamide, 2-(3-methoxy-azetidin-1-yl)-N-(7-methoxy-4-morpholin-4-yl-thiazolo[5,4-c]pyridin-2-yl)-isonicotinamide, and N-(7-methoxy-4-morpholin-4-yl-thiazolo[5,4-c]pyridin-2-yl)-2-morpholin-4-yl-isonicotinamide.

10. The compound of formula I in accordance with claim 1, wherein R$^1$ is selected from phenyl and R$^2$ is pyridyl, and pyridyl substituted by one or more substituents selected from morpholinyl and lower alkyl.

11. The compound of formula I in accordance with claim 10, wherein the compound is selected from N-(7-methoxy-4-phenyl-thiazolo[5,4-c]pyridin-2-yl)-2-morpholin-4-yl-isonicotinamide and N-(7-methoxy-4-phenyl-thiazolo[5,4-c]pyridin-2-yl)-2-methyl-isonicotinamide.

12. The compound of formula I in accordance with claim 1, wherein R$^1$ is morpholinyl and R$^2$ is selected from benzo[1,3]dioxole, and 2-oxa-5-aza-bicyclo [2.2.1]heptane.

13. The compound of formula I in accordance with claim 12, wherein the compound is selected from benzo[1,3]dioxole-5-carboxylic acid (7-methoxy-4-morpholin-4-yl-thiazolo[5,4-c]pyridin-2-yl)-amide, and (1S,4S)-2-oxa-5-aza-bicyclo [2.2.1]heptane-5-carboxylic acid (7-methoxy-4-morpholin-4-yl-thiazolo[5,4-c]pyridin-2-yl)-amide.

14. A process for preparing a compound of formula I

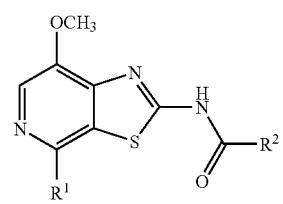

(I)

which process comprises reacting a compound of formula

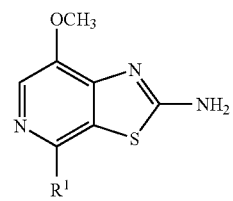

(7)

with a compound of formula

wherein,

R$^1$ is selected from morpholin-4-yl, phenyl and tetrahydropyran-4-yl;

R$^2$ is selected from

—(CH$_2$)$_n$-aryl;

—(CH$_2$)$_n$-aryl substituted by one or more substituents selected from the group consisting of halogen, lower alkoxy, lower alkyl, —(CH$_2$)$_n$NR'R", —O(CH$_2$)$_n$—O-lower alkyl, and —(CH$_2$)$_n$-heterocyclyl;

heteroaryl;
heteroaryl substituted by one or more substituents, selected from the group consisting of lower alkyl, lower alkoxy, —(CH$_2$)$_n$NR'R", —(CH$_2$)$_n$-heterocyclyl, and —(CH$_2$)$_n$-heterocyclyl substituted by one or more substituents selected from hydroxy, lower alkoxy, —(CH$_2$)$_n$—OH, —(CH$_2$)$_n$—O-lower alkyl and lower alkyl;
(CH$_2$)$_n$-cycloalkyl;
—(CH$_2$)$_n$—O-lower alkyl;
NR'R";
benzo[1,3]dioxole;
2-methyl-1-oxo-2,8-diaza-spiro [4,5] decane;
2-oxa-5-aza-bicyclo[2.2.1]heptane; or
1-oxa-8-aza-spiro[4.5]decane;
R' and R" are independently from each other selected from lower alkyl, —(CH$_2$)$_n$—O-lower alkyl, cycloalkyl, and cycloalkyl substituted by hydroxy; and n is 0, 1 or 2.

15. The process of claim 14, which further comprises converting the compound obtained into a pharmaceutically acceptable salt thereof.

16. A pharmaceutical composition which comprises a compound of formula I

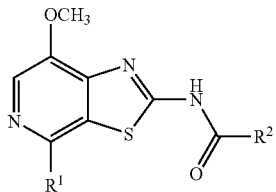

wherein,
R$^1$ is selected from morpholin-4-yl, phenyl and tetrahydropyran-4-yl;
R$^2$ is selected from
—(CH$_2$)$_n$-aryl;
—(CH$_2$)$_n$-aryl substituted by one or more substituents selected from the group consisting of halogen, lower alkoxy, lower alkyl, —(CH$_2$)$_n$NR'R", —O(CH$_2$)$_n$—O-lower alkyl, and —(CH$_2$)$_n$-heterocyclyl;
heteroaryl;
heteroaryl substituted by one or more substituents, selected from the group consisting of lower alkyl, lower alkoxy, —(CH$_2$)$_n$NR'R", —(CH$_2$)$_n$-heterocyclyl, and —(CH$_2$)$_n$-heterocyclyl substituted by one or more substituents selected from hydroxy, lower alkoxy, —(CH$_2$)$_n$—OH, —(CH$_2$)$_n$—O-lower alkyl and lower alkyl;
(CH$_2$)$_n$-cycloalkyl;
—(CH$_2$)$_n$—O-lower alkyl;
NR'R";
benzo [1,3]dioxole;
2-methyl-1-oxo-2,8-diaza-spiro[4,5]decane;
2-oxa-5-aza-bicyclo [2.2.1]heptane; or
1-oxa-8-aza-spiro[4.5]decane;
R' and R" are independently from each other selected from lower alkyl, —(CH$_2$)$_n$—O-lower alkyl, cycloalkyl, and cycloalkyl substituted by hydroxy; and n is 0, 1 or 2;
or a pharmaceutically acceptable salt thereof;
and a pharmaceutically acceptable excipient.

* * * * *